US011903971B2

(12) United States Patent
Moskowitz et al.

(10) Patent No.: US 11,903,971 B2
(45) Date of Patent: Feb. 20, 2024

(54) TREATMENT OF VON WILLEBRAND DISEASE

(71) Applicant: Cellphire, Inc., Rockville, MD (US)

(72) Inventors: Keith Andrew Moskowitz, Westfield, IN (US); Shan Xu, Rockville, MD (US); William Matthew Dickerson, Washington, DC (US); Amber Nicole Lee, Rockville, MD (US); Braden Carl Ishler, Gaithersburg, MD (US); Daniel Allen Sheik, Rockville, MD (US)

(73) Assignee: Cellphire, Inc., Rockville, MD (US)

( * ) Notice: Subject to any disclaimer, the term of this patent is extended or adjusted under 35 U.S.C. 154(b) by 0 days.

(21) Appl. No.: 17/166,490

(22) Filed: Feb. 3, 2021

(65) Prior Publication Data

US 2021/0315935 A1    Oct. 14, 2021

Related U.S. Application Data

(60) Provisional application No. 63/065,337, filed on Aug. 13, 2020, provisional application No. 62/980,850, filed on Feb. 24, 2020, provisional application No. 62/969,942, filed on Feb. 4, 2020.

(51) Int. Cl.
| | |
|---|---|
| *A61K 35/19* | (2015.01) |
| *A61K 9/19* | (2006.01) |
| *A61P 7/04* | (2006.01) |
| *A61K 31/195* | (2006.01) |
| *A61K 31/197* | (2006.01) |
| *A61K 38/36* | (2006.01) |
| *A61K 38/57* | (2006.01) |
| *A61K 9/50* | (2006.01) |
| *C12N 5/078* | (2010.01) |

(52) U.S. Cl.
CPC ............. *A61K 35/19* (2013.01); *A61K 9/19* (2013.01); *A61K 9/5068* (2013.01); *A61K 31/195* (2013.01); *A61K 31/197* (2013.01); *A61K 38/363* (2013.01); *A61K 38/57* (2013.01); *A61P 7/04* (2018.01); *C12N 5/0644* (2013.01)

(58) Field of Classification Search
CPC .................. A61K 35/19; A61K 9/19
See application file for complete search history.

(56) References Cited

U.S. PATENT DOCUMENTS

| | | |
|---|---|---|
| 3,928,566 A | 12/1975 | Briggs et al. |
| 3,932,943 A | 1/1976 | Briggs et al. |
| 4,059,967 A | 11/1977 | Rowe et al. |
| 4,157,383 A | 6/1979 | Sedlacek et al. |
| 4,455,299 A | 6/1984 | Grode |
| 4,481,189 A | 11/1984 | Prince |
| 4,670,013 A | 6/1987 | Barnes et al. |
| 4,865,871 A | 9/1989 | Livesey et al. |
| 4,994,367 A | 2/1991 | Bode |
| 5,059,518 A | 10/1991 | Kortright et al. |
| 5,213,814 A | 5/1993 | Goodrich |
| 5,332,578 A | 7/1994 | Chao |
| 5,364,756 A | 11/1994 | Livesey et al. |
| 5,423,738 A | 6/1995 | Robinson |
| 5,571,801 A | 11/1996 | Segall |
| 5,622,867 A | 4/1997 | Livesy |
| 5,656,498 A | 8/1997 | Iijima |
| 5,656,598 A | 8/1997 | Dunstan et al. |
| 5,723,281 A | 3/1998 | Segall et al. |
| 5,736,313 A | 4/1998 | Spargo |
| 5,759,542 A | 6/1998 | Gurewich |
| 5,800,978 A | 9/1998 | Goodrich |
| 5,817,381 A | 10/1998 | Chen |
| 5,827,741 A | 10/1998 | Beattie |
| 5,919,614 A | 7/1999 | Livesey |
| 5,958,670 A | 9/1999 | Goodrich |
| 5,993,804 A | 11/1999 | Read |
| 6,127,111 A | 10/2000 | Braun |
| 6,211,575 B1 | 4/2001 | Hansford |
| 6,221,575 B1 | 4/2001 | Roser |
| 6,372,423 B1 | 4/2002 | Braun |
| 6,596,296 B1 | 7/2003 | Nelson |
| 6,653,062 B1 | 11/2003 | DePablo |
| 6,723,497 B2 | 4/2004 | Wolkers |
| 6,770,478 B2 | 8/2004 | Crowe |
| 6,833,236 B1 | 12/2004 | Stienstra |
| 6,858,222 B2 | 2/2005 | Nelson |
| 7,033,603 B2 | 4/2006 | Nelson |
| 7,169,606 B2 | 1/2007 | DePablo |
| 7,514,095 B2 | 4/2009 | Nelson |

(Continued)

FOREIGN PATENT DOCUMENTS

| | | |
|---|---|---|
| CA | 1261259 A | 9/1989 |
| CA | 2097063 C | 6/1992 |

(Continued)

OTHER PUBLICATIONS

Swami et al., "von Willebrand Disease: A Concise Review and Update for the Practicing Physician", Clinical and Applied Thrombosis/Hemostasis, vol. 23(8), pp. 900-910. (Year: 2017).*

2.palomar.edu [online], "The Five Kingdoms Of Life," Feb. 1998, retrieved on May 17, 2021, retrieved from URL <https://www2.palomar.edu/users/warmstrong/trfeb98.htm>; 18 pages.

Appleman et al., "Cryopreservation of canine platelets," Journal of veterinary internal medicine, Jan. 2009, 23(1):138-145.

Clemmons et al., "Acquisition and aggregation of canine blood platelets: basic mechanisms of function and differences because of breed origin," American journal of veterinary research, Jan. 1, 1984, 45(1):137-144.

(Continued)

*Primary Examiner* — Michelle F. Paguio Frising
*Assistant Examiner* — Grant C Currens
(74) *Attorney, Agent, or Firm* — Double Helix Law; Emanuel Vacchiano

(57) ABSTRACT

Provided herein are methods and compositions for treating von Willebrand disease with platelets, platelet derivatives, and/or thrombosomes.

20 Claims, 3 Drawing Sheets

(56) References Cited

U.S. PATENT DOCUMENTS

| | | |
|---|---|---|
| 7,811,558 B2 | 10/2010 | Ho |
| 8,097,403 B2 | 1/2012 | Ho |
| 8,486,617 B2 | 7/2013 | Ho |
| 8,486,619 B2 | 7/2013 | Miller |
| 8,529,961 B2 | 9/2013 | Campbell |
| 8,877,060 B2 | 11/2014 | Sehal |
| 8,900,209 B2 | 12/2014 | Rosati |
| 9,402,866 B2 | 8/2016 | Radwanski et al. |
| 9,545,379 B2 | 1/2017 | Liu et al. |
| 9,863,699 B2 | 1/2018 | Corbin et al. |
| 9,878,011 B2 | 1/2018 | Landrigan et al. |
| 9,950,035 B2 | 4/2018 | Binder et al. |
| 10,400,017 B2 | 9/2019 | Higgins et al. |
| 10,441,634 B2 | 10/2019 | Landrigan et al. |
| 10,539,367 B2 | 1/2020 | Corbin et al. |
| 10,793,327 B2 | 10/2020 | Weimer et al. |
| 10,843,100 B2 | 11/2020 | Khan et al. |
| 10,969,171 B2 | 4/2021 | Corbin et al. |
| 10,976,105 B2 | 4/2021 | Corbin et al. |
| 11,052,045 B2 | 7/2021 | Liu et al. |
| 11,529,587 B2 | 12/2022 | Montgomery et al. |
| 11,701,388 B2 | 7/2023 | Moskowitz et al. |
| 11,752,468 B2 | 9/2023 | Montgomery et al. |
| 2001/0019819 A1 | 9/2001 | Wolkers et al. |
| 2001/0028880 A1 | 10/2001 | Fisher |
| 2001/0046487 A1 | 11/2001 | Roser et al. |
| 2002/0009500 A1 | 1/2002 | Wolkers et al. |
| 2002/0076445 A1 | 6/2002 | Crowe |
| 2003/0022333 A1 | 1/2003 | Bronshtein |
| 2003/0073238 A1 | 4/2003 | Dzekunov et al. |
| 2003/0148449 A1 | 8/2003 | Kuliopulos et al. |
| 2003/0157475 A1 | 8/2003 | Schenk |
| 2004/0136974 A1 | 7/2004 | Crowe |
| 2004/0147024 A1 | 7/2004 | Crowe |
| 2004/0152964 A1 | 8/2004 | Crowe |
| 2004/0185524 A1 | 9/2004 | Crowe |
| 2004/0265293 A1 | 12/2004 | Crowe et al. |
| 2005/0028559 A1 | 2/2005 | Hiromatsu |
| 2005/0048460 A1 | 3/2005 | Crowe |
| 2005/0074402 A1 | 4/2005 | Cagnolini |
| 2005/0181978 A1 | 8/2005 | Rojkjaer et al. |
| 2005/0191286 A1 | 9/2005 | Gandy |
| 2005/0222029 A1 | 10/2005 | Bartel et al. |
| 2006/0034809 A1 | 2/2006 | Ho et al. |
| 2006/0035383 A1 | 2/2006 | Ho |
| 2006/0051731 A1 | 3/2006 | Ho |
| 2006/0223050 A1 | 10/2006 | Crowe et al. |
| 2007/0087061 A1 | 4/2007 | Drake |
| 2007/0166389 A1 | 7/2007 | Bakaltcheva |
| 2007/0178104 A1 | 8/2007 | Awdalla |
| 2007/0243137 A1 | 10/2007 | Hainfeld |
| 2007/0243178 A1 | 10/2007 | Ho et al. |
| 2007/0248612 A1 | 10/2007 | Wilson |
| 2007/0249047 A1 | 10/2007 | McKenna, Jr. |
| 2008/0064628 A1 | 3/2008 | Goodall et al. |
| 2008/0145834 A1 | 6/2008 | Ho et al. |
| 2008/0286366 A1 | 11/2008 | Fischer et al. |
| 2008/0299212 A1 | 12/2008 | Kim |
| 2009/0035289 A1 | 2/2009 | Wagner et al. |
| 2009/0111118 A1 | 4/2009 | Mylvaganam et al. |
| 2009/0175905 A1 | 7/2009 | Tseng et al. |
| 2009/0299212 A1 | 12/2009 | Principe et al. |
| 2010/0055067 A1 | 3/2010 | Park |
| 2010/0135969 A1 | 6/2010 | Mishra |
| 2010/0159023 A1 | 6/2010 | Bjornstrup et al. |
| 2010/0190717 A1 | 7/2010 | Bevec |
| 2010/0196461 A1 | 8/2010 | Simpkins |
| 2010/0267928 A1 | 10/2010 | Heckl |
| 2010/0273141 A1 | 10/2010 | Bakaltcheva et al. |
| 2011/0008804 A1 | 1/2011 | Kain et al. |
| 2011/0027257 A1 | 2/2011 | Burnouf |
| 2011/0183311 A1 | 7/2011 | Ho |
| 2011/0189151 A1 | 8/2011 | Stossel et al. |
| 2012/0009221 A1 | 1/2012 | Hoerr et al. |
| 2012/0028236 A1 | 2/2012 | Sehgal |
| 2012/0095085 A1 | 4/2012 | Layzer et al. |
| 2012/0100522 A1 | 4/2012 | Saghbini et al. |
| 2012/0141434 A1 | 6/2012 | Peled et al. |
| 2012/0156306 A1 | 6/2012 | Weissman et al. |
| 2012/0264815 A1 | 10/2012 | Sullenger et al. |
| 2012/0276581 A1 | 11/2012 | Arav et al. |
| 2012/0321722 A1 | 12/2012 | Liu |
| 2013/0059380 A1 | 3/2013 | Ho et al. |
| 2013/0061849 A1 | 3/2013 | Lemper |
| 2013/0122107 A1 | 5/2013 | Bakaltcheva |
| 2013/0195959 A1 | 8/2013 | Patel |
| 2013/0210903 A1 | 8/2013 | Sullenger et al. |
| 2014/0037750 A1 | 2/2014 | Radwanski et al. |
| 2014/0065120 A1 | 3/2014 | Nichols |
| 2014/0329323 A1 | 11/2014 | Nygaard et al. |
| 2014/0330226 A1 | 11/2014 | Coffey |
| 2014/0356948 A1 | 12/2014 | Jeon et al. |
| 2015/0064259 A1 | 3/2015 | Simpkins et al. |
| 2015/0306212 A1 | 10/2015 | Kahvejian et al. |
| 2015/0313943 A1 | 11/2015 | Kishikawa et al. |
| 2015/0313944 A1 | 11/2015 | Feng et al. |
| 2015/0361453 A1 | 12/2015 | Gresele et al. |
| 2016/0082044 A1 | 3/2016 | Liu et al. |
| 2016/0206783 A1 | 7/2016 | Dietz |
| 2016/0219870 A1 | 8/2016 | Wang et al. |
| 2016/0231338 A1 | 8/2016 | Aster et al. |
| 2016/0235781 A1 | 8/2016 | Emanuele |
| 2016/0324897 A1 | 11/2016 | Ingber et al. |
| 2017/0198335 A1 | 7/2017 | Muller |
| 2017/0274012 A1 | 9/2017 | Bode et al. |
| 2017/0333593 A1 | 11/2017 | Willard |
| 2018/0009874 A1 | 1/2018 | Wilcox et al. |
| 2018/0070581 A1 | 3/2018 | Tarrand et al. |
| 2018/0092348 A1 | 4/2018 | She et al. |
| 2018/0169027 A1 | 6/2018 | Zhang et al. |
| 2018/0169139 A1 | 6/2018 | Feuerstein |
| 2018/0235894 A1 | 8/2018 | Gu et al. |
| 2018/0311176 A1 | 11/2018 | Ozsolak |
| 2018/0312903 A1 | 11/2018 | Grölz |
| 2019/0008143 A1 | 1/2019 | Dee |
| 2019/0076478 A1 | 3/2019 | Hale et al. |
| 2019/0192564 A1 | 6/2019 | Hijazi et al. |
| 2020/0046771 A1 | 2/2020 | Kuhn et al. |
| 2020/0060262 A1 | 2/2020 | Stolla |
| 2020/0076455 A1 | 3/2020 | Sharf |
| 2020/0078407 A1 | 3/2020 | Bhattacharya et al. |
| 2020/0093853 A1 | 3/2020 | Feuerstein |
| 2020/0206143 A1 | 7/2020 | Moskowitz et al. |
| 2020/0208109 A1 | 7/2020 | Moskowitz et al. |
| 2020/0208110 A1 | 7/2020 | Lee et al. |
| 2020/0224164 A1 | 7/2020 | Moskowitz et al. |
| 2020/0281980 A1 | 9/2020 | Willard et al. |
| 2020/0291356 A1 | 9/2020 | Jorda et al. |
| 2020/0346167 A1 | 11/2020 | Montgomery et al. |
| 2021/0046120 A1 | 2/2021 | Moskowitz et al. |
| 2021/0046121 A1 | 2/2021 | Moskowitz et al. |
| 2021/0069240 A1 | 3/2021 | Jorda et al. |
| 2021/0100846 A1 | 4/2021 | Lee et al. |
| 2021/0180016 A1 | 6/2021 | Moskowitz et al. |
| 2021/0189341 A1 | 6/2021 | Sheik et al. |
| 2021/0299179 A1 | 9/2021 | Moskowitz et al. |
| 2021/0308066 A1 | 10/2021 | Moskowitz et al. |
| 2021/0308185 A1 | 10/2021 | Moskowitz et al. |
| 2021/0353680 A1 | 11/2021 | Bhattacharya et al. |
| 2021/0368782 A1 | 12/2021 | Dee et al. |
| 2022/0168353 A1 | 6/2022 | Moskowitz et al. |
| 2022/0211029 A1 | 7/2022 | Moskowitz et al. |
| 2022/0273724 A1 | 9/2022 | Moskowitz et al. |
| 2022/0279777 A1 | 9/2022 | Moskowitz et al. |
| 2023/0112136 A1 | 4/2023 | Jorda et al. |
| 2023/0149467 A1 | 5/2023 | Montgomery et al. |
| 2023/0149468 A1 | 5/2023 | Antebi et al. |
| 2023/0158455 A1 | 5/2023 | Montgomery et al. |
| 2023/0226493 A1 | 7/2023 | Montgomery et al. |
| 2023/0248771 A1 | 8/2023 | Moskowitz et al. |

(56) References Cited

U.S. PATENT DOCUMENTS

| | | |
|---|---|---|
| 2023/0248772 A1 | 8/2023 | Willard |
| 2023/0285465 A1 | 9/2023 | Moskowitz et al. |

FOREIGN PATENT DOCUMENTS

| | | |
|---|---|---|
| CA | 2136848 A1 | 12/1993 |
| CA | 2393315 A1 | 6/2001 |
| CA | 2840568 A1 | 1/2013 |
| CA | 3053041 A1 | 2/2020 |
| CN | 103524613 | 1/2014 |
| CN | 103907595 | 7/2014 |
| CN | 108715834 A | 10/2018 |
| CN | 109942687 A | 6/2019 |
| EP | 0397890 A1 | 11/1990 |
| EP | 0967862 | 1/2003 |
| EP | 1374890 A2 | 1/2004 |
| EP | 1652538 | 5/2006 |
| EP | 1784639 A2 | 5/2007 |
| EP | 3681518 A1 | 7/2020 |
| EP | 3307283 B1 | 9/2020 |
| EP | 3551198 B1 | 2/2022 |
| JP | H08109136 | 4/1996 |
| JP | 2005053841 | 3/2005 |
| JP | 2012143554 A | 8/2012 |
| WO | WO 1990/005461 | 5/1990 |
| WO | 9012581 A1 | 11/1990 |
| WO | 1991017655 A1 | 11/1991 |
| WO | WO 1992008349 | 5/1992 |
| WO | WO 1993000806 | 1/1993 |
| WO | 1993023997 A1 | 12/1993 |
| WO | 9428950 A1 | 12/1994 |
| WO | 1998034478 A1 | 8/1998 |
| WO | 1999055346 A1 | 11/1999 |
| WO | 2001007921 A2 | 2/2001 |
| WO | 2001058266 A1 | 8/2001 |
| WO | 2003014305 A2 | 2/2003 |
| WO | 2003039582 A1 | 5/2003 |
| WO | 2003090839 A1 | 11/2003 |
| WO | WO 2004050896 | 6/2004 |
| WO | 2004078187 A1 | 9/2004 |
| WO | 2005002499 A2 | 1/2005 |
| WO | 2005020893 A2 | 3/2005 |
| WO | 2005021706 A2 | 3/2005 |
| WO | WO 2005077299 | 8/2005 |
| WO | 2005002499 A3 | 11/2005 |
| WO | WO 2006020773 | 2/2006 |
| WO | 2006059329 A1 | 6/2006 |
| WO | 2004050896 A3 | 12/2006 |
| WO | 2006020773 A3 | 7/2007 |
| WO | 2010046949 A1 | 4/2010 |
| WO | WO 2011020107 | 2/2011 |
| WO | 2011020107 A3 | 10/2011 |
| WO | 2012018484 A2 | 4/2012 |
| WO | 2012074637 A2 | 6/2012 |
| WO | 2014051537 A1 | 4/2014 |
| WO | WO 2014055949 | 4/2014 |
| WO | 2014066142 A1 | 5/2014 |
| WO | 2014118817 A2 | 8/2014 |
| WO | WO 2014118817 | 8/2014 |
| WO | 2015073587 A2 | 5/2015 |
| WO | 2015191632 A1 | 12/2015 |
| WO | WO 2016014854 | 1/2016 |
| WO | WO 2016057041 | 4/2016 |
| WO | 2016077682 A1 | 5/2016 |
| WO | 2016141325 A1 | 9/2016 |
| WO | 2016205144 A1 | 12/2016 |
| WO | WO 2016201081 | 12/2016 |
| WO | WO 2017040238 | 3/2017 |
| WO | 2017123539 A1 | 7/2017 |
| WO | WO 2018106250 | 6/2018 |
| WO | 2019055683 A1 | 3/2019 |
| WO | WO 2020023905 | 1/2020 |
| WO | 2020056009 A1 | 3/2020 |
| WO | WO 2020112963 | 6/2020 |
| WO | WO 2020113035 | 6/2020 |
| WO | WO 2020113090 | 6/2020 |
| WO | WO 2020113101 | 6/2020 |
| WO | 2020165152 A1 | 8/2020 |
| WO | 2020186193 A1 | 9/2020 |
| WO | 2020227149 A1 | 11/2020 |
| WO | 2021011857 A1 | 1/2021 |
| WO | 2021034716 A1 | 2/2021 |
| WO | 2021034719 A1 | 2/2021 |
| WO | 2021046409 A1 | 3/2021 |
| WO | 2021108538 A1 | 6/2021 |
| WO | 2021108539 A1 | 6/2021 |
| WO | 2021158622 A1 | 8/2021 |
| WO | 2021158625 A1 | 8/2021 |
| WO | 2021158641 A1 | 8/2021 |
| WO | 2021158645 A1 | 8/2021 |
| WO | 2021158646 A1 | 8/2021 |
| WO | 2021232015 A1 | 11/2021 |
| WO | 2022103861 A1 | 5/2022 |
| WO | 2022178177 A1 | 8/2022 |
| WO | 2022178191 A1 | 8/2022 |
| WO | 2022178177 A4 | 10/2022 |
| WO | 2023081804 A1 | 5/2023 |

OTHER PUBLICATIONS

Extended European Search report in EP Appln. No. 18856149.2, dated May 26, 2021, 9 pages.

Healthline.com [online], "How Many Cells Are in the Human Body? Fast Facts," Jul. 18, 2018, retrieved on May 17, 2021, retrieved from URL<https://www.https://www.healthline.com/health/number-of-cells-in-body>, 11 pages.

Lee et al., "Novel treatment modalities: New platelet preparations and subsititutes," British journal of haematology, Sep. 2001, 114(3):496-505.

microbenotes.com [online], "Types of Plant Cell—Definition, Structure, Functions, Diagrams," Feb. 25, 2020, retrieved May 17, 2021, retrieved from URL<microbenotes.com/types-of-plant-cell/>, 31 pages.

PCT International Preliminary Report on Patentability in PCT Appln. No. PCT/US2019/063549, dated Jun. 10, 2021, 9 pages.

PCT International Preliminary Report on Patentability in PCT Appln. No. PCT/US2019/063650, dated Jun. 10, 2021, 9 pages.

PCT International Preliminary Report on Patentability in PCT Appln. No. PCT/US2019/063750, dated Jun. 10, 2021, 8 pages.

PCT International Preliminary Report on Patentability in PCT Appln. No. PCT/US2019/063736, dated Jun. 10, 2021, 8 pages.

PCT International Search Report and Written Opinion in International Appln. No. PCT/US2021/016390, dated May 18, 2021, 13 pages.

PCT International Search Report and Written Opinion in PCT Appln. No. PCT/US2021/016360, dated May 21, 2021, 13 pages.

PCT International Search Report and Written Opinion in PCT Appln. No. PCT/US2021/016363, dated May 18, 2021, 15 pages.

PCT International Search Report and Written Opinion in PCT Appln. No. PCT/US2021/016389, dated May 18, 2021, 15 pages.

Scheinkönig et al., "Adoption of long-term cultures to evaluate the cryoprotective potential of trehalose for freezing hematopoietic stem cells," Bone marrow transplantation, Sep. 2004, 34(6):531-536.

PCT International Preliminary Report on Patentability in International Appln. No. PCT/US2019/050624, dated Mar. 25, 2021, 10 pages.

PCT International Search Report and Written Opinion for International Appln. No. PCT/US2020/62214, dated Mar. 17, 2021, 9 pages.

Abdelgawwad, et al., "Transfusion of platelets loaded with recombinant ADAMTS13 is efficacious for inhibiting arterial thrombosis in mice and in human," Arterioscler. Thromb. Vas. Biol., 2018, 38(11):2731-2743.

Adams, et al., "The principles of freeze-drying," DNA Repair Protocols, Methods in Molecular Biology, Humana Press, US, 2007, Chapter 2, 368:15-38.

Agam et al. "Passive Participation of Fixed Platelets in Aggregation Facilitated by Covalently Bound Fibrinogen" Blood 61:1, pp. 186-191, 1983.

(56) References Cited

OTHER PUBLICATIONS

Ahmadzada, et al., "Fundamentals of siRNA and miRNA therapeutics and a review of targeted nanoparticle delivery systems in breast cancer," Biophysical Reviews, 2018, 10:69-86.
Al Ghaithi, "Evaluation of the total Thrombus-Formation System (T-TAS)," Platelets, 2018, 1-8.
Arav, et al., "Freeze drying (lyophilization) of red blood cells," Journal of Trauma, 2011, 70:S61-S64.
Arnold P., et al., "The preparation and clinical administration of lyophilized platelet material to children with acute leukemia and aplastic anemia," The Journal of Pediatrics, 1956, 49(5):517-522.
Bynum, et al., "Evaluation of a lyophilized platelet-derived hemostatic product," Transfusion, 2019, 49:1490-1498.
Cellphire, "Loading Platelets with Biological Agents for Enhanced Local Delivery," 2006, 14 pages.
Chen et al., "Modifying murine von Willebrand factor A1 domain for in vivo assessment of human platelet therapies," Nature biotechnology, Jan. 2008, 26(1):114-119.
Chen, et al., "Advance of molecular imaging technology and targeted imaging agent in imaging and therapy," Biomed. Res. Int., 2014, 819324, 12 pages.
Chen, et al., "Stabilizaton of peptides against proteolysis through disulfide-bridged conjugation with synthetic aromatics," Org. Biomol. Chem., 2017, 15(8):1921-1929.
Christenson et al., "Autologous fibrin glue reinforced by platelets in surgery of ascending aorta", Thorac. Cardiovasc. Surg., vol. 52, p. 225-229, 2004.
Christopher, et al., "MicroRNA therapeutics: discovering novel targets and developing specific therapy," Perspect. Clin. Res., 2016, 7(2):68-74.
Cox, et al., "Platelets and the innate immune system: mechanisms of bacterial-induced platelet activation," Journal of Thrombosis and Haemostasis, 2011, 9:1097-1107.
Cryoprotein. The American Heritage® Stedman's Medical Dictionary. Houghton Mifflin Company. Mar. 24, 2010. <Dictionary.com http://dictionary.reference.com/browse/cryoprotein>, 2 pages.
Daidone, "Usefulness of the Total Thrombus-formation Analysis System (T-TAS) in the diagnosis and characterization of von Willebrand disease," Haemophillia, 2016, 22:949-956.
Daly, et al., "Hemostatic regulators of tumor angiogenesis: a source of antiangiogenic agents for cancer treatment?" Journal of the National Cancer Institute, 2003, 95(22):1660-1673.
Dennison, "A simple and universal method for making up buffer solutions," Biochem. Edu., 1988, 16(4):210-211.
diapharma.com [online], "DiaPharmaProductList," retrieved on Feb. 18, 2021, retrieved from URL<http://diapharma.com/wp-content/uploads/2016/03/DiaPharmaProductList_ML-00-00002REV7.pdf>, 4 pages.
Dielis, et al., "Coagulation factors and the protein C system as determinants of thrombin generation in a normal population," J. Thromb. Haemost., 2008, 6:125-131.
Diener, "Antiplatelet agents and randomized trials," Review in Neurological Diseases, 2007, 4(4):177-183.
Dong, et al., "Ristocetin-dependent, but not botrocetin-dependent, binding of von Willebrand factor to the platelet glycoprotein Ib-IX-V complex correlates with shear-dependent interactions," Blood, 2001, 97:162-168.
European Search Report in EP Appln. No. 05784165.2, dated Mar. 26, 2008, 6 pages.
European Search Report in EP Appln. No. 16808270.9, dated Nov. 22, 2018, 4 pages.
European Search Report in EP Appln. No. 16842662.5, dated Jul. 26, 2019, 14 pages.
Expose, http://dictionary.reference.com/browse/expose, accessed Jul. 18, 2009, 2 pages.
Extended European Search report in EP Appln. No. 16923314.5, dated Jun. 18, 2020, 7 pages.
Extended European Search Report in EP Appln. No. 17738796.6, dated Jul. 23, 2019, 7 pages.

Fijnheer et al., "Platelet activation during preparation of platelet concentrates: a comparison of the platelet-rich plasma and the buffy coat methods," Transfusion, 1990, 30(7):634-638.
Fischer et al., "Primary and secondary hemostatic functionalities of rehydrated, lyophilized platelets," 2006, Transfusion, 46:1943-1950.
Fitzpatrick, et al., "Thrombosomes: a platelet-derived hemostatic agent for control of noncompressible hemorrhage," Transfusion, 2013, 53:100S-106S.
Gaertner et al., "Migrating platelets are mechano-scavengers that collect and bundle bacteria," Cell, Nov. 30, 2017, 171(6):1368-1382.
Gilbert et al., "Platelet-derived microparticles express high affinity receptors for factor VIII.", J.Biol.Chem., 1991, 266:17261-17268.
Giles et al., "A combination of factor Xa and phosphatidylcholine-phosphatidylserine vesicles bypasses factor VIII in vivo", Br. J., Haematol., 1988, 69(4):491-497.
Greene, et al., "Chapter 9: Component Preparation and Manufacturing," Transfusion Medicine and Hemostasis, Elsevier Science, 2009, pp. 45-50.
Heitz, et al., "Twenty years of cell-penetrating peptides: from molecular mechanisms to therapeutics," British Journal of Pharmacology, 2009, 157:195-206.
helena.com [online], "Ristocetin Cofactor Assay," retrieved on Feb. 18, 2021, retrieved from URL <https://www.helena.com/Procedures/Pro064Rev5.pdf>, 2 pages.
Hemker, et al., "Calibrated automated thrombin generation measurement in clotting plasma," Pathophysiol. Haemost. Thromb., 2003, 33:4-15.
Hoffman et al., "Coagulation Factor IXa Binding to Activated Platelets and Platelet-Derived Microparticles: A Flow Cytometric Study," Thromb. Haemost., 1992, 68:74-78.
Holcomb, et al., "Optimal fluid therapy for traumatic hemorrhagic shock," Crit. Care Clin., 2017, 33(1):15-36, Author: Chang et al.
Holme et al., "Platelet-derived microvesicles and activated platelets express factor Xa activity," Blood Coagul. Fibrinolysis, 1995, 6:302-310.
Homepage.haemonetics.com [online], "TEG® 5000 Thrombelastograph® Hemostasis Analyzer System," retrieved Feb. 18, 2021, retrieved from URL<http://homepage.haemonetics.com/en/products/devices/surgical-and-diagnostic-devices/teg-5000>, 3 pages.
Hong, et al., "Transfection of human platelets with short interfering RNA," Clin. Transl. Sci., 2011, 4(3):180-182.
Hrachovinova et al., "Interaction of P-selectin and PSGL-1 generates microparticles that correct hemostasis in a mouse model of hemophilia A," Nat Med., 2003, 9(8): 1020-1025.
Ishler, "StablePlate RX Canine Promotes in vitro Thromblin Generation and Thrombus Formation Under High Shear," Journal of Veterinary Internal Medicine, 2019 ACVIM Forum Research Abstract Program, p. 2483, Abstract Only.
Ito, et al., "Total Thrombus-formation Analysis System (T-TAS) can predict periprocedural bleeding events in patients undergoing catheter ablation for atrial fibrillation," Journal of American Heart Association, 2015, 5(1):e002744, 12 pages.
Kariko, et al., "Phosphate-enhanced transfection of cationic lipid-complexed mRNA and plasmid DNA," Biochim. Biophys. Acta, 1998, 1369(2):320-334.
Kerrigan, "Platelet interactions with bacteria," The non-thrombotic role of platelets in health and disease; Chapter 4, 2015, 65-84.
Kerrigan, et al., "Molecular basis for *Staphylococcus aureus* mediated platelet aggregate formation under arterial shear in vitro," Arteriosclerosis Thrombosis and Vascular Biology, 2008, 28(2):334-340.
Kirby et al., "Preparation of liposomes containing Factor VIII for oral treatment of haemophilia," 1984, J. Microencapsul. 1(1): 33-45.
Kishbaugh et al., "Intervening with Platelet Therapies," NEHL at the National Zoo, 2017, vol. 4 #2, 4 Pages.
Lam, et al., "siRNA versus miRNA as therapeutics for gene silencing," Molecular Therapy—Nucleic Acids, 2015, 4:e252.
Lannan, et. al., "Breaking the Mold: Transcription Factors in the Anuceleate Platelet and Platelet-Derived Microparticles," Front Imunnol., 2015, 6:48, 17 pages.

(56) References Cited

OTHER PUBLICATIONS

Luo et al., "Construction and in vitro studies of magnetic-apoferritin nanocages conjugated with KGDS peptide targeted at activated platelets for the MRI diagnosis of thrombus," Journal of Nanoparticle Research, Aug. 2019, 21(8):1-12.

Makielski, et al., "Development and implementation of a novel immune thrombocytopenia bleeding score for dogs," J. Vet. Intern. Med., 2018, 32(3):1-10.

Mazzucco et al., "The use of autologous platelet gel to treat difficult-to-heal wounds: a pilot study," Transfusion, 2004, 44:1013-1018.

MedWow, "Manufacturer Specifications—CS-2000 Plus, Baxter," Apr. 19, 2011, retrieved on Sep. 26, 2019 from http://www.medwow.com/med/apheresis-machine/baxter/cs-3000-plus/5782.model-spec, 2 pages.

Merten et al., "Platelet Microparticles Promote Platelet Interaction with Subendothelial Matrix in a Glycoprotein lib/IIIa Dependent Mechanism", Circulation, 1999, 99:2577-2582.

Miajlovic, et al., "Both complement- and fibrinogen-dependent mechanisms contribute to platelet aggregation mediated by *Staphylococcus aureus* clumping factor B," Infection and Immunity, 2007, 75(7):3335-3343.

Mishra et al., "Cell-penetrating peptides and peptide nucleic acid-coupled MRI contrast agents: evaluation of cellular delivery and target binding," Bioconjugate chemistry, Oct. 21, 2009, 20(10):1860-1868.

Montecinos, et al., "Selective targeting of bioengineered platelets to prostate cancer vasculature: new paradigm for the therapeutic modalities," 2015, 19(7):1530-1537.

Morris, et al., "A peptide carrier for the delivery of biologically active proteins into mammalian cells," Nature Biotechnology, 2001, 19:1173-1176.

Morrison et al. "Storage of apheresis platelet concentrates after manual replacement of >95% of plasma with PAS 5, Vox Sangunis," May 2014, 107(3):247-253.

Natan, et al., "Freeze-drying of mononuclear cells derived from umbilical cord blood followed by colony formation," PLoS One, 2009, 4(4):e5240.

Nieuwland et al., "Cell-derived microparticles generated in patients during cardiopulmonary bypass are highly procoagulant", Circulation, 1997, 96:3534-3541.

Novakowski, et. al., "Delivery of mRNA to platelets using lipid nanoparticles," Scientific Reports, 2019, 9:552, 11 pages.

O'Brien, et al., "Multiple mechanisms for the activation of human platelet aggregation by *Staphylococcus aureus*: roles for the clumping factors ClfA and ClfB, the serine-aspartate repeat protein SdrE and protein A," Molecular Microbiology, 2002, 44(4):1033-1044.

Oikarinen et al., "Augmentation of the narrow traumatized anterior alveolar ridge to facilitate dental implant placement," Dent. Traumatol., 2003, 19:19-29.

Oliver, "Dry state preservation of nucleated cells: progress and challenge," Cryobiology, 2011, 63(3):307, abstract.

PCT International Preliminary Report on Patentability in International Appln. No. PCT/US2017/012836, dated Jul. 17, 2018, 7 pages.

PCT International Preliminary Report on Patentability in International Appln. No. PCT/US2005/28559, dated May 8, 2007, 5 pages.

PCT International Preliminary Report on Patentability in International Appln. No. PCT/US2015/060533, dated May 16, 2017, 5 pages.

PCT International Preliminary Report on Patentability in International Appln. No. PCT/US2016/036657, dated Dec. 12, 2017, 6 pages.

PCT International Preliminary Report on Patentability in International Appln. No. PCT/US2016/048846, dated Mar. 6, 2018, 5 pages.

PCT International Preliminary Report on Patentability in International Appln. No. PCT/US2016/065681, dated Jun. 11, 2019, 7 pages.

PCT International Preliminary Report on Patentability in International Appln. No. PCT/US2019/043723, dated Feb. 11, 2021, 14 pages.

PCT International Preliminary Report on Patentability in PCT Appln. No. PCT/US2018/050924, dated Mar. 17, 2020, 17 pages.

PCT International Search Report and Written Opinion in International Appln. No. PCT/US2005/28559, dated Mar. 23, 2007, 3 pages.

PCT International Search Report and Written Opinion in International Appln. No. PCT/US2015/060533, dated Jan. 28, 2016, dated Feb. 25, 2016—1 page.

PCT International Search Report and Written opinion in International Appln. No. PCT/US2016/036657, dated Aug. 29, 2016, 7 pages.

PCT International Search Report and Written Opinion in International Appln. No. PCT/US2016/048846, dated Nov. 16, 2016, 2 pages.

PCT International Search Report and Written Opinion in International Appln. No. PCT/US2016/065681, dated Feb. 17, 2017, 2 pages.

PCT International Search Report and Written Opinion in International Appln. No. PCT/US2017/012836, dated Apr. 7, 2017, 8 pages.

PCT International Search Report and Written Opinion in International Appln. No. PCT/US2018/050924, dated Nov. 20, 2018, 18 pages.

PCT International Search Report and Written Opinion in International Appln. No. PCT/US2020/042492, dated Nov. 24, 2020, 9 pages.

PCT International Search Report and Written Opinion in International Appln. No. PCT/US2020/046522, dated Nov. 10, 2020, 10 Pages.

PCT International Search Report and Written Opinion in International Appln. No. PCT/US2020/046525, dated Nov. 10, 2020, 11 Pages.

PCT International Search Report and Written Opinion in International Appln. No. PCT/US2020/049489, dated Feb. 16, 2021, 8 Pages.

PCT International Search Report and Written Opinion in International Appln. No. PCT/US2020/062216, dated Feb. 9, 2021, 9 pages.

PCT International Search Report and Written Opinion in International Appln. No. PCT/US2019/043723, dated Oct. 9, 2019, 16 pages.

PCT International Search Report and Written Opinion in PCT Appln. No. PCT/US2019/050624, dated Nov. 20, 2019, 23 pages.

PCT International Search Report and Written Opinion in PCT Appln. No. PCT/US2019/063549, dated Feb. 4, 2020, 10 pages.

PCT International Search Report and Written Opinion in PCT Appln. No. PCT/US2019/063650, dated Feb. 27, 2020, 11 pages.

PCT International Search Report and Written Opinion in PCT Appln. No. PCT/US2019/063736, dated Feb. 20, 2020, 10 pages.

PCT International Search Report and Written Opinion in PCT Appln. No. PCT/US2019/063750, dated Feb. 19, 2020, 10 pages.

PCT International Search Report and Written Opinion in PCT Appln. No. PCT/US2020/022705, dated Jul. 29, 2020, 12 pages.

PCT International Search Report and Written Opinion in PCT Appln. No. PCT/US2020/031172, dated Aug. 12, 2020, 9 pages.

PCT Invitation to Pay Additional Fees in PCT Appln. No. PCT/US2020/022705, dated May 18, 2020, 2 pages.

Pierce et al., "Platelet-derived growth factor and transforming growth factor-beta enhance tissue repair activities by unique mechanisms", J. Cell Biol., 1989, 109:429-440.

Platelet. The American Heritage® Dictionary of the English Language, Fourth Edition. Houghton Mifflin Company, 2004. Mar. 23, 2010. <Dictionary.com http://dictionary.reference.com/browse/platelet>, 2 pages.

Prior et al., "A Sprayable Hemostat Containing Fibrillar Collagen, Bovine Thrombin, and Autologous Plasma", Ann.Thorac.Surg., 1999, 68:479-485.

Robson et al., "Coronavirus RNA proofreading: molecular basis and therapeutic targeting," Molecular Cell, Aug. 4, 2020, 18 Pages.

(56) References Cited

OTHER PUBLICATIONS

Rosing et al., "Impaired factor X and prothrombin activation associated with decreased phospholipid exposure in platelets from a patient with a bleeding disorder", Blood, 1985, 65:1557-1561.
Rounding. Dictionary.com. Dictionary.com Unabridged (v 1.1 ). Random House, Inc. http://dictionary.reference.com/browse/rounding (accessed: Oct. 27, 2008), 4 pages.
Rowley, et. al., "Platelet mRNA: the meaning behind the message," Curr. Opin. Hematol., 2012, 19(5):385-391.
scbcinfo.org [online], Strong, ed., "Indications for platelet transfusion therapy," available on or before Dec. 25, 2005, via Internet Archive: Wayback Machine URL <https://web.archive.org/web/20051225110714/http://www.scbcinfo.org/publications/bulletin_v2_n2.htm>, 7 pages.
Serebruany, et al., "Crossreactivity of Human versus Swine Platelet Surface Antigens Is Similar for Glycoproteins Ib and IIIa, but Not for the Glycoprotein IIb/IIIa Complex," J.Thromb. and Thromb., 1998, 5:37-41.
Sims et al., "Complement Proteins C5b-9 Cause Release of Membrane Vesicles from the Platelet Surface That Are Enriched in the Membrane Receptor for Coagulation Factor Va and Express Prothrombinase Activiy", J. Biol Chem., 1988, 263:18205-18212.
Sims et al., "Regulatory control of complement on blood platelets. Modulation of platelet procoagulant responses by a membrane inhibitor of the C5b-9 complex", J Biol. Chem., 1989, 264:19228-19235.
Steed, "The role of growth factors in wound healing," Surg. Clin. North Am., 1997, 77:575-586.
Strober, "Trypan blue exclusion test of cell viability," Current Protocols in Immunology, 1997, A.3B.1-A.3B.2.
Szekely and Lex, "Antifibrinolytics," Heart, Lung and Vessels, 2014, 6(1):5-7.
Tacar, et al., "Doxorubicin: an update on anticancer molecular action, toxicity and novel drug delivery systems," The Journal of Pharmacy and Pharmacology, 2013, 65(2):157-170.
Tans et al., "Comparison of anticoagulant and procoagulant activities of stimulated platelets and platelet-derived microparticles", Blood, 1991, 77:2641-2648.
Taune, et al., "Whole blood coagulation assays ROTEM and T-TAS to monitor dabigatran t dabigatran treatment," Thrombosis Research, 2017, 153(30):76-82.
thrombinoscope.com [online], "Thrombin Calibrator," retrieved on Feb. 18, 2021, retrieved from URL <https://www.thrombinoscope.com/method-products/products/>, 2 pages.
Tsegaye et al., "Platelet activation suppresses HIV-1 infection of T cells," Retrovirology, 2013, 10:48.
T-TAS.info [online], Publications, 2019, retrieved on Aug. 28, 2019, retrieved from URL<https://www.t-tas.info/pub/>, 8 pages.
Ullah et al., "A Review on Malarial Parasite," World Journal of Zoology, 2015, 10(4):285-290.
Valentini, et al., "Use of CD9 and CD61 for the characterization of AML-M7 by flow cytometry in a dog," Vet. Comp. Oncol., 2011, 10:312-318.
Valeri, et al., "Survival of baboon biotin-X-N-hydroxysuccinimide and 111In-oxine-labelled autologous fresh and lyophilized reconstituted platelets," Vox Sanguinis, 2005, 88:122-129.
Vlieghe, et al., "Synthetic therapeutic peptides: science and market," Drug Discovery Today, 2010, 15:40-56.
Volz, et al., "Inhibition of platelet GPVI induces intratumor hemorrhage and increases efficacy of chemotherapy in mice," Blood, 2019, 133(25):2696-2706.
Wajon et al., "Intraoperative Plateletpheresis and Autologous Platelet Gel Do Not Reduce Chest Tube Drainage or Allogeneic Blood Transfusion After Reoperative Coronary Artery Bypass Graft", Anesth. Analg., 2001, 93:536-542.
Wang, et al., "Commonly used dietary supplements on coagulation function during surgery," Medicines, 2015, 2:157-185.
Whitney et al. "Ratiometric Activatable Cell-Penetrating Peptides Provide Rapid In Vivo Readout of Thrombin Activation," Angewandte Chemie International Edition, 2013, 52:325-330.

Wilkerson, M.J., et al., "Platelet size, platelet surface-associated IgG, and reticulated platelets in dogs with immune-mediated thrombocytopenia," Veterinary Clinical Pathology, 2001, 30(3):141-149.
Wilson, et al., "A simple rapid method for layering blood on Ficoll-Isopaque gradients," Journal of Immunological Methods, 1975, 9(1): 67-68.
Wolkers et al., "Human Platelets Loaded with Trehalose Survive Freeze-Drying", Cryobiology 42:79-87, 2001.
WPI Database No. AN 2014-E98028 / CN103524613, Jan. 22, 2014: 2 pages.
Xu, et al., "Doxorubicin-loaded platelets as a smart drug delivery system: an improved therapy for lymphoma," Scientific Reports, 2017, 7:42632.
Yarovoi et al., "Factor VIII ectopically expressed in platelets: efficacy in hemophilia A treatment", Blood 102(12): 4006-4013, 2003.
Zhou, et. al., "Loading Trehalose into Red Blood Cells by Improved Hypotonic Method," Cell Preservation Technology, 2008, 6(2):119-122.
Powner, et. al., "Counteracting The Effects Of Anticoagulants And Antiplatelet Agents During Neurosurgical Emergencies", Neurosurgery, vol. 57, No. 5, Nov. 2005 pp. 823-831.
Read, et. al., "Preservation of hemostatic and structural properties of rehydrated lyophilized platelets: potential for long-term storage of dried platelets for transfusion", Proceedings of the National Academy of Sciences of the USA, vol. 92, Jan. 1995, pp. 397-401, DOI: 10.1073/pnas.92.2.397.
Reddoch et al., "Extended Storage of Refrigerated Platelets in Isoplate and Intersol PAS: An Evaluation of Two FDA-Approved Methods of Collection", Blood, vol. 128, Issue 22, Dec. 2, 2016, 3 pages, doi.org/10.1182/blood.V128.22.2631.2631.
Samanbar et al., "Evaluation Of The Hemostatic Ability of The New Device 'Total Thrombus Formation Analysis System' (T-TAS) for Thrombocytopeniatients. Invitro effect of lyophilized human platelets", Cellphire, Inc. Jul. 2022, 1 page, Poster.
Sane, et. al., "Bleeding During Thrombolytic Therapy For Acute Myocardial Infarction: Mechanisms and Management", Annals Of Internal Medicine, vol. 111, No. 12, Dec. 15, 1989, pp. 1010-1022.
Schoug, et.al., "Differential effects of polymers PVP90 and Ficoll400 on storage stability and viability of Lactobacillus coryniformis Si3 freeze-dried in sucrose", Journal of Applied Microbiology, vol. 108, No. 3, pp. 1032-1040, Feb. 8, 2010.
Sheik et al., "Stably Loading Human Platelets with Gadolinium Conjugates to Enhance Magnetic Resonance Imaging", Cellphire, Inc., 2020,1 page.
Sibbing, et. al., "Antiplatelet effects of clopidogrel and bleeding in patients undergoing coronary stent placement", Journal of Thrombosis and Haemostasis, vol. 8, Issue 2, pp. 250-256, DOI: 10.1111/j.1538-7836.2009.03709.x.
Srivastava, et. al., "The rebirth of the contact pathway: a new therapeutic target", Current Opinion in Hematology, vol. 27, No. 5, Sep. 2020, pp. 311-319, doi: 10.1097/MOH.0000000000000603.
Sum et al., "Wound-healing properties of trehalose-stabilized freeze-dried outdated platelets", Transfusion, vol. 47, Issue 4, Apr. 2007, pp. 672-679, doi: 10.1111/j.1537-2995.2007.01170.x.
Tang, et. al., "Targeted repair of heart injury by stem cells fused with platelet nanovesicles", Nature Biomedical Engineering, vol. 2, No. 1, May 30, 2018, pp. 17-26, DOI:10.1038/s41551-017-0182-x.
Trivedi, et. al., "Freeze-Dried Platelets Promote Clot Formation, Attenuate Endothelial Cell Permeability, And Decrease Pulmonary Vascular Leak In A Murine Model Of Hemorrhagic Shock", The Journal of Trauma and Acute Care Surgery, vol. 90, Issue 2, Feb. 1, 2021, pp. 203-214, doi: 10.1097/TA.0000000000002984.
Tsai etal, "Increased risk of bleeding in patients on clopidogrel therapy after drug-eluting stents implantation: insights from the HMO Research Network-Stent Registry (HMORN-stent)", Circulation Cardiovascular Interventions, vol. 3, Issue 3, Jun. 1, 2010, pp. 230-235, DOI: 10.1161/CIRCINTERVENTIONS.109.919001.
Undas et al., "Antithrombotic properties of aspirin and resistance to aspirin: beyond strictly antiplatelet actions", Blood, vol. 109, No. 6, Mar. 15, 2007, pp. 2285-2292, DOI: 10.1182/blood-2006-01-010645.

(56) References Cited

OTHER PUBLICATIONS

Valeri et al., "Freezing human platelets with 6 percent dimethyl sulfoxide with removal of the supernatant solution before freezing and storage at—80° C. without post thaw processing" Transfusion, vol. 45 (12), Dec. 2005, pp. 1890-1898, DOI: 10.1111/j.1537-2995. 2005.00647.x.
Van Der Meer et al, Platelet preservation: Agitation and containers, Transfusion and Apheresis Science, vol. 44, Issue 3, Jun. 2011, pp. 297-304, //doi.org/10.1016/j.transci.2011.03.005.
Van Der Meijden et al., "Platelet- and erythrocyte-derived microparticles trigger thrombin generation via factor XIIa", Journal of Thrombosis and Haemostasis, vol. 10, Issue 7, Apr. 26, 2012, pp. 1355-1362, doi.org/10.1111/j.1538-7836.2012.04758.x.
Vibhudutta et al., "Trehalose Stabilized Freeze Dried Human Platelets, Thrombosomes, Reduce Blood Loss In Thrombocytopeniabbit Ear Bleed Model By As Much As 89.5%", Cellphire, Inc. P-0454, www.bodevet.com, Mar. 2017, 1 page, Poster.
Vibhudutta et al., "Trehalose Stabilized Freeze Dried Human Platelets, Thrombosomes, Persist In Circulation 24 Hours After Infusion and Are Non-Immunogenic In New Zealand White Rabbits", International Society of Blood Transfusion Vox Sanguinis, vol. 99, Suppl. 1, P-0454, 2010, p. 262, Abstract.
Vibhudutta et al., "Trehalose Stabilized Freeze Dried Human Platelets, Thrombosomes, Persist In Circulation 24 Hours After Infusion and Are Non-Immunogenic In New Zealand White Rabbits", Cellphire, Inc. P-0454, 1 page, Poster.
Vibhudutta et al., "Trehalose Stabilized Freeze Dried Human Platelets, Thrombosomes, Reduce Blood Loss In Thrombocytopenic Rabbit Ear Bleed Model By As Much As 89.5%", International Society of Blood Transfusion Vox Sanguinis, vol. 99, Suppl. 1, P-0452, 2010, p. 261, Abstract.
Viswanathan et al., "Clopidogrel Alters Thrombus Quantity and Quality in Patients With Type II Diabetes Mellitus and Stable Coronary Artery Disease", Journal of the American College of Cardiology, vol. 61, No. 10, Mar. 2013, E1154, 1 page.
Wei et al., "ICAM-5/Telencephalin Is a Functional Entry Receptor for Enterovirus D68", Cell Host Microbe, vol. 20, Issue 5, Nov. 9, 2016, pp. 631-641, doi: 10.1016/j.chom.2016.09.013.
Whitman et al., "Design of the CRYPTICS Trail: A Randomized Controlled Trial Comparing Cryopreserved to Liquid Stored Platelets in Patients Undergoing Cardiac Surgery", Journal of Thoracic and Cardiovascular Surgery, 2022, doi.org/10.1016/j.xjon.2022.11. 003.
Wickramasinghe, "Washing Cryopreserved Blood Products Using Hollow Fibres", Food and Bioproducts Processing, vol. 77, Issue 4, Dec. 1999, pp. 287-292, DOI:org/10.1205/096030899532574.
Wright et al., "Doxorubicin delivery via novel lyophilized/reconstituted platelet-product has anti-cancer activity", Hematology & Transfusion International Journal, vol. 9, Issue 3, 2021, pp. 41-51.
Xu et al., "EACA Loaded Platelets Sustain Clots More Efficiently Than Free EACA", Cellphire, Inc., Jul. 2021, 1 page, Poster.
Xu et al., "EACA Loaded Platelets Sustain Clots More Efficiently Then Free EACA", Cellphire, Inc., 2021. 2 page.
Xu et al., "Human Platelet Derived Lyophilized Hemostatic Retains Hemostatic Properties Heparin Complexation with Protamine", Cellphire, Inc. Jul. 2022, 1 page, Poster.
Xu et al., "Thrombosomes As a Treatment Option for Low-Dose Heparin Reversal", Cellphire Therapeutics, Inc., Rockville, MD, 2020 Annual Meeting, 3 pages.
Zafar et. al., "Badimon Perfusion Chamber: An Ex Vivo Model of Thrombosis", Methods Molecular Biology, vol. 1816, 2018, pp. 161-171, doi: 10.1007/978-1-4939-8597-5_12.
Zhou et al., "Hemostatic and Thrombogenic Properties of Lyophilized Human Platelets", CellPhire, Inc. Jul. 2021, 1 page, Poster.
Zhou et al., "Lyophilized Human Platelets Promote Coagulation in Humanized Mouse VWF Transgenic Models of Hemostasis and Thrombosis", Cellphire, Inc., 2021, 1 page.
Ghaithi et al., "Evaluation of the Total Thrombus-Formation System (T-TAS): application to human and mouse blood analysis", Platelets, vol. 30, Issue 7, 2019, pp. 893-900, doi: 10.1080/09537104. 2018.1535704.
International Partial Search Report in International Appln No. PCT/US2022/016866, dated May 11, 2022, 13 pages.
International Preliminary Report on Patentability in International Appln. No. PCT/US2019/050624, dated Mar. 9, 2021, 10 pages.
International Preliminary Report on Patentability in International Appln. No. PCT/US2019/063549, dated Jun. 10, 2021, 9 pages.
International Preliminary Report on Patentability in International Appln. No. PCT/US2019/063650, dated Jun. 10, 2021, 9 pages.
International Preliminary Report on Patentability in International Appln. No. PCT/US2019/063736, dated Jun. 10, 2021, 8 pages.
International Preliminary Report on Patentability in International Appln. No. PCT/US2019/063750, dated Jun. 10, 2021, 8 pages.
International Search Report and Written Opinion in International Appln. No. PCT/US2020/062214, dated Mar. 17, 2021, 8 pages.
International Search Report and Written Opinion in International Appln. No. PCT/US2021/032783, dated Aug. 24, 2021, 13 pages.
International Search Report and Written Opinion in International Appln. No. PCT/US2021/058814, dated Mar. 17, 2020, 14 pages.
International Search Report and Written Opinion in International Appln. No. PCT/US2022/016866, dated Jul. 4, 2022, 18 pages.
International Search Report and Written Opinion in International Appln. No. PCT/US2022/016883, dated May 11, 2022.
Ishler et al., "Lyophilized Human Platelets Interact with Fresh Platelets to Promote Hemostasis Under Shear In Vitro", Cellphire, Inc., 2021, 2 page, Abstract.
Ishler et al., "Lyophilized Human Platelets Interact with Fresh Platelets to Promote Hemostasis Under Shear In Vitro", Cellphire, Inc., PB0990, Jul. 2021, 1 page, Poster.
Ishler et al., "Lyophilized Human Platelets Show Hemostatic Function Independent of von Willebrand Factor", Abstract No. PB1533, ISth 2020 Virtual Congress Presentation, Jul. 2020, Res Pract Thromb Haemost. 2020; 4 (Suppl 1). https://abstracts.isth.org/abstract/lyophilized-human-platelets-show-hemostatic-function-independent-of-von-willebrand-factor/.
Ishler et al., "Lyophilized Platelets Show Hemostatic Function Independent of von Willebrand Factor", Cellphire, Inc., Department of Discovery and Research, ISth 2020 Virtual Congress, PB1533, Jul. 2020, 1 page, Poster.
Ishler et al., "StablePlate RX® Canine Promotes In Vitro Thrombin Generation and Thrombus Formation Under High Shear", Cellphire, Inc., 2019, 1 page, Poster1.
Ishler et al., "StablePlate RX® Canine Promotes In Vitro Thrombin Generation and Thrombus Formation Under High Shear", Cellphire, Inc., 2019, 1 page, Poster2.
Jennings et al., "Antiplatelet and anticoagulant agents: Key differences in mechanisms of action, clinical application, and therapeutic benefit in patients with non-ST-segment-elevation acute coronary syndromes", Current Opinion in Cardiology vol. 23, No. 4, Jul. 2008, pp. 302-308, DOI: 10.1097/HCO.0b013e3283021ad9.
Jennings et al., "The pharmacodynamics of parenteral glycoprotein IIb/IIIa inhibitors", Journal of Interventional Cardiology, vol. 15, No. 1, Feb. 2002, pp. 45-60, DOI: 10.1111/j.1540-8183.2002. tb01034.x.
Joshi et al., "Lyophilised Reconstituted Human Platelets Increase Thrombus Formation In A Clinical Ex Vivo Model Of Deep Arterial Injury", Thrombosis and Haemostasis, vol. 108, No. 1, 2012, pp. 176-182, DOI: 10.1160/TH12-02-0059.
Joshi et al., "Thrombosomes Show Dose-Dependent Increase in Thrombus Formation in a Model of Deep Arterial Injury", Blood, vol. 118, Issue 21, Nov. 18, 2011, Abstract 2319, 8 pages, doi.org/10.1182/blood.V118.21.2319.2319.
Kuhn et al., "Assessing Circulation Persistence of Human Platelet Products in a NOD-SCID Mouse Model", Cellphire, Inc. Jul. 2022, 1 page, Poster.
Lassila et. al., "Dynamic Monitoring of Platelet Deposition on Severely Damaged Vessel Wall in Flowing Blood. Effects of Different Stenoses on Thrombus Growth", Arteriosclerosis, vol. 10, No. 2, Mar.-Apr. 1990, pp. 306-315, doi: 10.1161/01.atv.10.2.306.

(56) References Cited

OTHER PUBLICATIONS

Lee et al., "High Efficiency Transfection and Preservation of Platelets with Tumor Suppressing Short RNA", Cellphire, Inc. Jul. 2020, 1 page, Poster.
Lee et al., "Lyophilized Human Platelets Exhibit Adhesive Interactions with *Staphylococcus aureus*", Cellphire, Inc. Jul. 2020, 1 page, Poster.
Li et al., "Extended antiplatelet therapy with clopidogrel alone versus clopidogrel plus aspirin after completion of 9- to 12-month dual antiplatelet therapy for acute coronary syndrome patients with both high bleeding and ischemic risk. Rationale and design of the OPT-BIRISK double-blinded, placebo-controlled randomized trial", American Hear Journal, vol. 228, Oct. 2020, pp. 1-7, https://doi.org/10.1016/j.ahj.2020.07.005.
Lo et al., "Development of a multi-compartment microfiltration device for particle fractionation" 16th International Conference on Miniaturized Systems for Chemistry and Life Sciences, MicroTAS 2012—Okinawa, Japan, Oct. 28, 2012-Nov. 1, 2012, 3 pages.
Lucking et. al., "Characterisation and reproducibility of a human ex vivo model of thrombosis", Thrombosis Research, vol. 126, No. 5, Nov. 2010, pp. 431-435, doi: 10.1016/j.thromres.2010.06.030.
Machine Language Translation of Chinese Patent No. CN108715834 A Titled [EN], "A Kind of Platelet Lysates Liquid and Preparation Method There of Rich in CD41+, CD81+ Micro-Capsule", Oct. 30, 2018, 10 pages.
Machine Language Translation of Japanese Patent JP2012143554 A2 Titled "[EN] Polysulfone-Based Hollow Fiber Membrane, Hollow Fiber Membrane Module for Cleaning Platelet Suspension, and Cleaning Method of Platelet Suspension.", Aug. 2, 2012, 33 pages.
Mailer et al., "Commentary on "Pharmacological profile of asundexian, a novel, orally bioavailable inhibitor of factor XIa": Small molecule factor XIa inhibitor asundexian allows for safer anticoagulation", Journal of Thrombosis and Haemostasis, vol. 20, Issue 6, Jun. 2022, pp. 1309-1311, https://doi.org/10.1111/jth.15722.
Marder, "Bleeding Complications Of Thrombolytic Treatment", American Journal of Hospital Pharmacy, vol. 47, Suppl 2, Sep. 1990, pp. S15-S19.
Marris, "The war against wounds", Nature, Mar. 21, 2007, Issue 446, pp. 369-371.
Mathews et al., "Development of Lyophilized Platelet-Derived Extracellular Vesicles for Multiple Indications", Cellphire, Inc., Oct. 2020, 1 page, Poster.
Mathews et al., "Development of Lyophilized Platelet-Derived Extracellular Vesicles for Multiple Indications", Chellphire, Inc., 2020, 1 page, Abstract.
McCarrel, et. al., "Temporal Growth Factor Release from Platelet-Rich Plasma, Trehalose Lyophilized Platelets, and Bone Marrow Aspirate and Their Effect on Tendon and Ligament Gene Expression" Journal of Orthopaedic Research : Official Publication of the Orthopaedic Research Society, vol. 27(8), Aug. 1, 2009, pp. 1033-1042,DOI: 10.1002/jor.20853.
Mehendale, et. al., "Platelet Enrichment From Whole Blood In A Clog-Free Microfluidic Radial Pillar Device (RAPID)", Biomedical Microdevices, bioRxiv, Oct. 4, 2017, DOI: https://doi.org/10.1101/197749.
Mehendale, et. at., "Platelet Enrichment In A Continuous And Clog-Free Microfluidic Filter With Sunflower Head Geometry", 20th International Conference on Miniaturized Systems for Chemistry and Life Sciences, Dublin, Ireland, Oct. 9-13, 2016, pp. 272-273.
Meisel et. al., "A Simplified Direct Lipid Mixing Lipoplex Preparation: Comparison of Liposomal-, Dimethylsulfoxide-, and Ethanol-Based Methods", Scientific Reports, vol. 6, Article 27662, Jun. 21, 2016, 12 pages, doi: 10.1038/srep27662.
Midgett et al., "Combination of freeze-dry microscopy, differential scanning calorimetry, and electron microscopy analysis as a guide for lyophilization cycle optimization to enhance Thrombosomes function", Cryobiology, vol. 63, Issue 3, 2011, p. 320, Abstract, doi: 10.1016/j.cryobiol.2011.09.054.

Mihatov, et. al., "Individualizing Dual Antiplatelet Therapy (DAPT) Duration Based on Bleeding Risk, Ischemic Risk, or Both: An Analysis From the DAPT Study", Cardiovascular Revascularization Medicine, vol. 41, Aug. 2022, pp. 105-112, https://doi.org/10.1016/j.carrev.2022.01.006.
Montague, "Strategies To Improve Haemostasis In Trauma: Evaluation Of Thrombosomes In The Presence Of Native Platelet Dysfunction", vol. 100, Issue Suppl 3, 2014, pp. A91-A92, DOI:10.1136/heartjnl-2014-306118.158.
Moskowitz et al., "Hemostatic Properties of Infusible Trehalose-Stabilized Lyophilized Platelet Derivatives", Blood, vol. 104, Issue 11, Nov. 16, 2004, p. 834, Abstract, doi.org/10.1182/blood.V104.11.834.834.
Moskowitz, "Thrombosomes for the Treatment of Bleeding Associated with Aggressive Anticoagulation", Cellphire, Inc., Dec. 2021, 40 pages, Posters.
Müller et. al., "Factor XI and XII as antithrombotic targets", Current Opinion In Hematology, vol. 15, No. 5, Sep. 2011, pp. 349-355, doi: 10.1097/MOH.0b013e3283497e61.
Mullin, et.al., "Doxorubicin chemotherapy for presumptive cardiac hemangiosarcoma in dogs", Veterinary and Comparative Oncology, vol. 14, Issue 4, Dec. 18, 2014, 13 pages, doi:10.1111/vco.12131.
NasrEldin, "Effect of cold storage on platelets quality stored in a small containers: Implications for pediatric transfusion", Pediatric Hematology Oncology Journal, vol. 2, Issue 2, Aug. 2017, pp. 29-34, doi.org/10.1016/j.phoj.2017.07.001.
Ohanian, et. al., "Freeze-Dried Platelets Are A Promising Alternative In Bleeding Thrombocytopeniatients with Hematological Malignancies", American Journal of Hematology, vol. 97, Issue 3, Mar. 1, 2022, pp. 256-266, doi: 10.1002/ajh.26403.
Pati et al., "Targeting the Endotheliopathy of Trauma in Hemorrhagic Shock and Traumatic Brain Injury with Freeze-Dried Platelets", Defense Technical Information Center, U.S. Army Medical Research and Development Command, Medicine and Medical Research; Biology, Sep. 1, 2020, 22 pages.
Pietramaggiori, et. al., "Trehalose Lyophilized Platelets For Wound Healing", Wound Repair And Regeneration : Official Publication Of The Wound Healing Society [and] the European Tissue Repair Society, vol. 15 (2), Mar. 9, 2007, pp. 213-220. doi:10.1111/j.1524-475X.2007.00207.x.
Alquwaizani, et.al., "Anticoagulants: A Review of the Pharmacology, Dosing, and Complications", Current Emergency and Hospital Medicine Reports, vol. 1, No. 2, Apr. 21, 2013, pp. 83-97, DOI: 10.1007/s40138-013-0014-6.
Bannai et al., "The effects of pH and agitation on platelet preservation", The Journal Of AABB Transfusion, vol. 25, Jan.-Feb. 1985, pp. 57-59, https://doi.org/10.1046/j.1537-2995.1985.25185116505.x.
Barroso, et. al., "Safety Evaluation Of A Lyophilized Platelet Derived Hemostatic Product", Transfusion, vol. 58 (12), Dec. 2018, pp. 2969-2977, DOI: 10.1111/trf.14972.
Böck et al., "Cryopreservation of human platelets with dimethyl sulfoxide: changes in biochemistry and cell function", Transfusion, vol. 35, No. 11, Nov.-Dec. 1995, pp. 921-924, doi: 10.1046/j.1537-2995.1995.351196110896.x.
Bohoněk, Miloš. "Cryopreservation of Platelets: Advances and Current Practice." Cryopreservation Biotechnology in Biomedical and Biological Sciences, Chapter 4. IntechOpen, Dec. 7, 2018, pp. 47-70.
Booth et al., "Lyophilized human platelets are superior to apheresis or fresh-drawn platelets in their ability to accelerate thrombin production", Cellphire, Inc. Jul. 2022, 1 page, Poster.
Cap, et. al., "Trauma Induced Coagulopathy", Chapter 22: Platelet Transfusion, Springer International Publishing, 2016, pp. 347-376.
Charkhkar et al., "Amyloid beta modulation of neuronal network activity in vitro", Brain Research, vol. 1629, Dec. 2015, pp. 1-9, doi: 10.1016/j.brainres.2015.09.036.
Chelliah et. al., "P-selectin antagonism reduces thrombus formation in humans", Journal of Thrombosis and Haemostasis, vol. 7, No. 11, Nov. 2009, pp. 1915-1919. doi: 10.1111/j.1538-7836.2009.03587.x.
Colman, "Are hemostasis and thrombosis two sides of the same coin?", Journal of Experimental Medicine, Mar. 20, 2006, vol. 203, No. 3, pp. 493-495, doi: 10.1084/jem.20060217.

(56) References Cited

OTHER PUBLICATIONS

Cowles, "Anticoagulant effect of aspirin goes beyond platelet aggregation", Hematology/Oncology, May 1, 2007, 3 pages.
Crowe et al., "Freeze-dried platelets: Moving towards clinical use", Cryobiology, vol. 66, Issue 3, Jun. 2013, p. 348, Abstract, doi.org/10.1016/j.cryobiol.2013.02.028.
Crowe et. al., "Stabilization of Dry Mammalian Cells: Lessons from Nature", Integrative and Comparative Biology, vol. 45, Issue 5, Nov. 2005, pp. 810-820, https://doi.org/10.1093/icb/45.5.810.
Crowe, et. al., "Stabilization of membranes in human platelets freeze-dried with trehalose", Chemistry and Physics of Lipids, vol. 122, Issues 1-2, Jan. 2003, pp. 41-52, https://doi.org/10.1016/S0009-3084(02)00177-9.
Dee et al., "Trehalose Stabilized Freeze Dried Human Platelets, Thrombosomes, Express Surface Markers, Thromboelastogram (TEG) Values And Size Distribution Similar To Two To Three Day Old Stored Platelets", International Society of Blood Transfusion Vox Sanguinis, vol. 99, Suppl. 1, P-0453, 2010, p. 262, Abstract.
Dee et al., "Trehalose Stabilized Freeze Dried Human Platelets, Thrombosomes, Express Surface Markers, Thromboelastogram (TEG) Values And Size Distribution Similar To Two To Three Day Old Stored Platelets", Cellphire, Inc., P-0453, 2019, 1 page, Poster.
Dickerson et al., "Lyophilized Human Platelets Restore Hemostasis in the Presence of the P2Y12 Inhibitors Cangrelor, Ticagrelor and Clopidogrel", Cellphire, Inc., 2020, 6 pages, Poster.
Dickerson et al., "Lyophilized Human Platelets Restore Hemostasis in the Presence of the P2Y12 Inhibitors Cangrelor, Ticagrelor and Clopidogrel", Cellphire Therapeutics Inc., Rockville, MD, 7 pages, Poster.
Dickerson et al., "Lyophilized Human Platelets Restore Hemostasis in the Presence of the P2Y12 Inhibitors Cangrelor, Ticagrelor and Clopidogre", American Society of Hematology, Blood, 3.22 Disorders Of Coagulation Or Fibrinolysis, Nov. 5, 2020, 6 pages.
Dickerson et al., "Lyophilized human platelets support thrombosis unlike normal platelets in the presence of GPIIb/IIIa antagonists", Cellphire Therapeutics, ISth Virtual Congress, Jul. 2021, 1 page, Poster.
Dickerson et al., "Lyophilized human platelets support thrombosis unlike normal platelets in the presence of GPIIb/IIIa antagonists", Cellphire, Inc., AS-ISTH-2021-01436, 2021. 2 pages, Abstract.
Dickerson et al., "Thrombosomes As a Treatment Option for Low-Dose Heparin Reversal", Cellphire, Inc, Oct. 2020. 1 page, Poster.
Dickson et al., "A scalable, micropore, platelet rich plasma separation device." Biomedical Microdevices, vol. 14 (6), Jul. 2012, pp. 1095-1102. DOI:10.1007/s10544-012-9675-2.
Dinçer et al., "Effect of taurine on wound healing", Amino Acids, vol. 10, Issue 1, Mar. 1996, pp. 59-71, doi: 10.1007/BF00806093.
Dumont, et. al, "A randomized controlled trial evaluating recovery and survival of 6% dimethyl sulfoxide-frozen autologous platelets in healthy volunteers", Transfusion vol. 53(1), Jan. 2013, pp. 128-137.
Eikelboom, et. al., "Combined antiplatelet and anticoagulant therapy clinical benefits and risks", Journal of Thrombosis and Haemostasis, vol. 5, Suppl 1, Jul. 2007, pp. 255-263, DOI: 10.1111/j.1538-7836.2007.02499.x.
Etchill, et. al., "Platelet Transfusion In Critical Care And Surgery: Evidence-Based Review Of Contemporary Practice And Future Directions", Shock, vol. 47, No. 5, May 1, 2017, pp. 537-549.
Extended European Search Report in EP Appln. No. 19840600.1 dated Mar. 25, 2022.
Extended European Search Report in EP Appln. No. 19888909.9 dated Sep. 28, 2022.
Extended European Search Report in EP Appln. No. 19888994.1 dated Nov. 7, 2022.
Extended European Search Report in EP Appln. No. 19891082.0 dated Sep. 30, 2022.
Extended European Search Report in EP Appln. No. 20769409.2 dated Dec. 6, 2022.
Extended European Search Report in EP Appln. No. 20802506.4 dated Jan. 4, 2023.
Fischer et al., "The interaction of factor VIIa with rehydrated, lyophilized platelets", Platelets, vol. 19 (3), May 2008, pp. 182-191, DOI:10.1080/09537100701493794.
Fischer et. al., "Thrombus Formation with Rehydrated, Lyophilized Platelets", Hematology (Amsterdam, Netherlands), vol. 7 (6), Dec. 2002, pp. 359-369, DOI:10.1080/1024533021000047954.
Fitzpatrick et al., "A Novel Lyophilized Platelet Derivative Produces Effective Hemostasis in Uncontrolled Bleeding/Shock Model without Systemic Thrombosis", Blood, vol. 118, Issue 21, Nov. 18, 2011, pp. 719-722, doi.org/10.1182/blood.V118.21.719.719.
Fitzpatrick et al., "Freeze-dried platelets: Advancing towards clinical use", Cryobiology, vol. 67, Issue 3, Dec. 2013, p. 420, Abstract, doi.org/10.1016/j.cryobiol.2013.09.086.
Fitzpatrick et al., "Stabilization and preservation of a platelet derived hemostatic agent, Thrombosomes", Cryobiology, vol. 63, Issue 3, Dec. 2011, p. 306, Abstract, doi:10.1016/j.cryobiol.2011.09.005.
Fitzpatrick, "Novel platelet products under development for the treatment of thrombocytopenia or acute hemorrhage", Transfusion and Apheresis Science, vol. 58, Issue 1, Feb. 2019, pp. 7-11, doi: 10.1016/j.transci.2018.12.010.
Gao et al., "Development of Optimal Techniques for Cryopreservation of Human Platelets: I. Platelet activation during cold storage (at 22 and 8° C.) and cryopreservation", Cryobiology vol. 38(3), May 1999, pp. 225-235, DOI: 10.1006/cryo.1999.2162.
Godier et al., "Management of antiplatelet therapy for non elective invasive procedures of bleeding complications: proposals from the French working group on perioperative haemostasis (GIHP), in collaboration with the French Society of Anaesthesia and Intensive Care Medicine (SFAR)" Anaesthesia, Critical Care and Pain Medicine, vol. 38, Issue 3, Jun. 2019, pp. 289-302, doi: 10.1016/j.accpm.2018.10.004.
Goggs, et. al., "Lyophilized Platelets Versus Cryopreserved Platelets For Management Of Bleeding In Thrombocytopeniaogs: A Multicenter Randomized Clinical Trial", Journal Of Veterinary Internal Medicine, Nov. 2020, vol. 34, Issue 6, pp. 2384-2397, doi: 10.1111/jvim.15922.
Grosset et al., "Rapid presymptomatic detection of PrPSc via conformationally responsive palindromic PrP peptides", Peptides, vol. 26, Issue 11, Nov. 2005, pp. 2193-2200, doi: 10.1016/j.peptides.2005.03.006.
Hagedorn, et. al., "Factor XIIa Inhibitor Recombinant Human Albumin Infestin-4 Abolishes Occlusive Arterial Thrombus Formation Without Affecting Bleeding", Circulation, vol. 121, Issue 13, Apr. 6, 2010, pp. 1510-1517, DOI: 10.1161/CIRCULATIONAHA.109.924761.
Hale et al., "A Novel Use Of the NOD SCID Mouse Model for Hemostatic Efficacy", Cellphire, Inc., 2019, 1 page.
Heitmeier et al., "Pharmacological profile of asundexian, a novel, orally bioavailable inhibitor of factor XIa", Journal of Thrombosis and Haemostasis, vol. 20, No. 6, Jun. 2022, pp. 1400-1411, https://doi.org/10.1111/jth.15700.
Holmes, et. al., "Combining Antiplatelet and Anticoagulant Therapies", Journal of The American College of Cardiology, vol. 54, No. 2, Jul. 7, 2009, pp. 95-109.
Huebner et al., "Freeze-dried plasma enhances clot formation and inhibits fibrinolysis in the presence of tissue plasminogen activator similar to pooled liquid plasma", Transfusion, vol. 57, Issue 8, Aug. 2017, pp. 2007-2015, DOI:10.1111/trf.14149.
Human Translation of Chinese patent No. CN103907595 Published Jul. 9, 2014, Trehalose-containing platelet low temperature preservation solution and application thereof, First Inventor Zhao Shuming.
Inaba et al., "Dried platelets in a swine model of liver injury", Shock, vol. 41, Issue 5, May 2014, pp. 429-434, doi: 10.1097/SHK.0000000000000141.
Booth et al., "Lyophilized human platelets are superior to apheresis or fresh-drawn platelets in their ability to accelerate thrombin production", Cellphire, Inc. Jul. 2022, 1 page, abstract.

(56) References Cited

OTHER PUBLICATIONS

Bullok, et al., "Permeation Peptide Conjugates for In Vivo Molecular Imaging Applications", Molecular Imaging, Jan.-Mar. 2006, vol. 5, Issue 1, pp. 1-15.

Chen et al., "Expanding the Potential of Doxorubicin-Loaded Cryopreserved Platelets for Targeted Cancer Drug Delivery", Cellphire, Inc., 21st International Drug Delivery and Nanomedicines Symposium, Sep. 15-17, 2023, 1 page, poster.

Chen et al., "Stabilized Platelets: A Drug Delivery System for Potential Human Hepatocellular Carcinoma Therapy", Cellphire, Inc. ISth 2023, Montréal, Jun. 24-28, 2023, 1 page, poster.

Extended European Search Report in EP Appln. No. 19860896.0 dated Jun. 14, 2023.

Gybel-Brask et al., "Freeze-dried platelets (Thrombosomes®) reverses CPB-induced platelet dysfunction ex-vivo", RegionH, Rigshospitalet, The Center of Diagnostic Investigations, 2023, 1 page, poster.

International Partial Search Report in International Appln No. PCT/US2022/079280, dated Feb. 20, 2023, 14 pages.

International Search Report and Written Opinion in International Appln No. PCT/US2022/079280, dated Apr. 21, 2023, 27 pages.

International Search Report and Written Opinion in International Appln. No. PCT/US2023/066904, dated Sep. 12, 2023, 12 pages.

International Search Report and Written Opinion in International Appln. No. PCT/US2023/066965, dated Aug. 4, 2023, 10 pages.

Kuhn et al., "Mechanism of Action of a Freeze-dried Platelet-derived Hemostatic Product", Cellphire, Inc. Cellular Therapeutics in Trauma and Critical Care, May 8-11, 2023, 1 page, poster.

Machine Language Translation of Chinese Patent No. CN109942687 A, Shen et at., Titled [EN], "68Ga Marks EACA Modification c-Met Molecular Imaging Probe And Preparation And Application", Jun. 28, 2019, 10 pages.

Millipore Sigma, "Dulbecco's Modified Eagle's Medium (DMEM)Formulation", Merck KGaA, Sigma-Aldrich Solutions, 2023, 15 pages, retreived from https://www.sigmaaldrich.com/US/en/technical-documents/technical-article/cell-culture-and-cell-culture-analysis/mammalian-cell-culture/dulbecco-modified-eagle-medium-formulation.

Ogiwara, et al., "Procoagulant Activity of Antifibrinolytic Agents; A Novel Hemostatic Mechanism of Tranexamic Acid and Epsilon-Aminocaproic Acid", Blood, Nov. 19, 2010, vol. 116, Issue 21, Abstract 1151, 3 pages, https://doi.org/10.1182/blood.V116.21.1151.1151.

Pan, et al., "Wound healing monitoring using near infrared fluorescent fibrinogen", Biomedical Optics Express, Jul. 27, 2010, vol. 1, Issue 1, pp. 285-294, doi: 10.1364/boe.1.000285.

Pietramaggiori et al., "Freeze-dried platelet-rich plasma shows beneficial healing properties in chronic wounds", Wound Repair And Regeneration, vol. 14, Issue 5, Sep. 29, 2006, pp. 573-580, doi.org/10.1111/j.1743-6109.2006.00164.x.

Reuss et al., "Intracellular delivery of carbohydrates into mammalian cells through swelling-activated pathways", The Journal Of Membrane Biology, vol. 200, Issue 2, Jul. 15, 2004, pp. 67-81, doi: 10.1007/s00232-004-0694-7.

Sheik et al., "Stably Loading Human Platelets with Gadolinium Conjugates to Enhance Magnetic Resonance Imaging", Cellphire, Inc., 2020, 3 pages, poster.

Török et al., "Preservation of Trehalose-Loaded Red Blood Cells by Lyophilization", Cell Preservation Technology, vol. 3, No. 2, Jul. 11, 2005, pp. 96-11, doi.org/10.1089/cpt.2005.3.96.

U.S. Appl. No. 17/166,487 Non-Final Office Action dated May 8, 2023.

U.S. Appl. No. 17/166,648 Non-Final Office Action dated Jul. 28, 2023.

Wang et al., "Solubility and Molecular Interactions of Trimetazidine Hydrochloride in 12 Monosolvents and Solvent Mixtures of Methanol + (Ethanol, N,N-Dimethylformamide or Ethyl Acetate)", Journal Of Chemical Engineering Data, Folume 63, Sep. 6, 2018, pp. 3704-3714, doi.org/10.1021/acs.jced.8b00235.

Wikström et al., "Viability of freeze dried microencapsulated human retinal pigment epithelial cells", European Journal Of Pharmaceutical Sciences, vol. 47, Issue 2, Sep. 29, 2012, pp. 520-526, doi: 10.1016/j.ejps.2012.06.014.

Zhang et al., "Coupling of liquid chromatography with mass spectrometry by desorption electrospray ionization (DESI)", Chemical Communications, Issue 14, Feb. 28, 2011, pp. 4171-4173, doi.org/10.1039/C0CC05736C.

\* cited by examiner

TREATMENT OF VON WILLEBRAND DISEASE

CROSS-REFERENCE TO RELATED APPLICATIONS

This application claims priority to U.S. Provisional Patent Application No. 62/969,942, filed on Feb. 4, 2020, U.S. Provisional Patent Application No. 62/980,850, filed on Feb. 24, 2020, and U.S. Provisional Patent Application No. 63/065,337, filed on Aug. 13, 2020, the contents of which are incorporated herein by reference in their entireties.

TECHNICAL FIELD

Provided herein, are methods of treating conditions, such von Willebrand disease with platelets, platelet derivatives, and/or thrombosomes. In some embodiments, the platelets, platelet derivatives, and/or thrombosomes are loaded with anti-fibrinolytic compounds.

Anti-fibrinolytic loaded platelets described herein can be stored under typical ambient conditions, refrigerated, cryopreserved, for example with dimethyl sulfoxide (DMSO), and/or lyophilized after stabilization (e.g., to form thrombosomes)

BACKGROUND

Blood is a complex mixture of numerous components. In general, blood can be described as comprising four main parts: red blood cells, white blood cells, platelets, and plasma. The first three are cellular or cell-like components, whereas the fourth (plasma) is a liquid component comprising a wide and variable mixture of salts, proteins, and other factors necessary for numerous bodily functions. The components of blood can be separated from each other by various methods. In general, differential centrifugation is most commonly used currently to separate the different components of blood based on size and, in some applications, density.

Unactivated platelets, which are also commonly referred to as thrombocytes, are small, often irregularly-shaped (e.g., discoidal or ovoidal) megakaryocyte-derived components of blood that are involved in the clotting process. They aid in protecting the body from excessive blood loss due not only to trauma or injury, but to normal physiological activity as well.

Platelets are considered crucial in normal hemostasis, providing the first line of defense against blood escaping from injured blood vessels. Platelets generally function by adhering to the lining of broken blood vessels, in the process becoming activated, changing to an amorphous shape, and interacting with components of the clotting system that are present in plasma or are released by the platelets themselves or other components of the blood. Purified platelets have found use in treating subjects with low platelet count (thrombocytopenia) and abnormal platelet function (thrombasthenia). Concentrated platelets are often used to control bleeding after injury or during acquired platelet function defects or deficiencies, for example those occurring during surgery and those due to the presence of platelet inhibitors.

SUMMARY OF THE INVENTION

Provided herein are methods and compositions that can be used to treat Von Willebrand disease (VWD) with thrombosomes (e.g., unloaded thrombosomes). Also, provided herein are methods of treating von Willebrand disease in a subject, including administering a therapeutically effective amount of anti-fibrinolytic loaded platelets to the subject in need thereof. Also provided herein are methods of treating von Willebrand disease where the method does not comprise administering an anti-fibrinolytic (or other therapeutic agent).

Provided herein are methods of treating a hemorrhage in a subject, including administering a therapeutically effective amount of anti-fibrinolytic loaded platelets to the subject in need thereof.

In some embodiments of any of the methods provided herein, the concentration of the therapeutically effective amount of anti-fibrinolytic loaded into the platelets is from about 100 μM to about 10 mM.

In some embodiments of any of the methods described herein, the anti-fibrinolytic is selected from the group including of ε-aminocaproic acid, aprotinin, aminomethylbenzoic acid, tranexamic acid, and fibrinogen.

In some embodiments, the anti-fibrinolytic is ε-aminocaproic acid. In some embodiments, the ε-aminocaproic acid is present in a concentration from about 1 μM to about 100 mM.

Also provided herein are methods of treating a hemorrhage in a subject, including administering a therapeutically effective amount of unloaded thrombosomes to the subject in need thereof. In some embodiments of treating a hemorrhage in a subject, the concentration of the therapeutically effective amount of unloaded thrombosomes is from about $1 \times 10^2$ particles/kg to about $1 \times 10^{13}$ particles/kg.

In some embodiments of treating a coagulopathy in a subject, the composition is administered following administration to the subject an antiplatelet agent or an anticoagulant, or a subject having Von Willebrand disease.

Also provided herein are methods of treating von Willebrand disease in a subject, the method comprising: administering a therapeutically effective amount of freeze-dried platelets to the subject in need thereof.

Also provided herein are methods of treating von Willebrand disease in a subject, the method comprising: administering a therapeutically effective amount of freeze-dried platelets to the subject, wherein the method does not comprise administering an anti-fibrinolytic.

In some embodiments, the von Willebrand disease is von Willebrand disease type 1, von Willebrand disease type 2, or von Willebrand disease type 3. In some embodiments, the von Willebrand disease is acquired von Willebrand disease.

In some the concentration of the therapeutically effective amount of freeze-dried platelets is from about $1 \times 10^2$ particles/kg to about $1 \times 10^{13}$ particles/kg. In some embodiments, the concentration of the therapeutically effective amount of freeze-dried platelets is from about $1 \times 10^4$ to about $1 \times 10^{11}$ particles/kg. In some embodiments, the concentration of the therapeutically effective amount of freeze-dried platelets is from about $1 \times 10^6$ to about $1 \times 10^9$ particles/kg. In some embodiments, the concentration of the therapeutically effective amount of freeze-dried platelets is at least $8.5 \times 10^8$ particles/kg. In some embodiments, the concentration of the therapeutically effective amount of freeze-dried platelets is at least $8.49 \times 10^9$ particles/kg.

In some embodiments, the surface expression of CD42b on the therapeutically effective amount of freeze-dried platelets is about 50% less than the surface expression of CD42b on platelets. In some embodiments, the surface expression of CD42b on the therapeutically effective amount of freeze-dried platelets is about 40% less than the surface expression of CD42b on platelets. In some embodiments, the surface expression of CD42b on the therapeutically effective amount of freeze-dried platelets is about 25% less than the surface expression of CD42b on platelets. In some embodiments, the therapeutically effective amount of freeze-dried platelets forms clots in von Willebrand factor deficient plasma.

In some embodiments, the therapeutically effective amount of freeze-dried platelets are administered topically. In some embodiments, the therapeutically effective amount of freeze-dried platelets are administered intravenously. In some embodiments, therapeutically effective amount of freeze-dried platelets are administered intramuscularly. In some embodiments, the therapeutically effective amount of freeze-dried platelets are administered subcutaneously.

Also provided herein are methods of treating a coagulopathy in a subject, the method comprising administering to the subject in need thereof an effective amount of a composition comprising platelets or platelet derivatives and an incubating agent comprising one or more salts, a buffer, optionally a cryoprotectant, and optionally an organic solvent, wherein the composition is administered to the subject having von Willebrand disease.

Also provided herein are methods of treating a coagulopathy in a subject, the method comprising administering to the subject in need thereof a therapeutically effective amount of a composition prepared by a process comprising incubating platelets with an incubating agent comprising one or more salts, a buffer, optionally a cryoprotectant, and optionally an organic solvent, to form the composition, wherein the composition is administered to the subject having von Willebrand disease.

In some embodiments, the von Willebrand disease is von Willebrand disease type 1, von Willebrand disease type 2, von Willebrand disease type 3, or acquired von Willebrand disease.

DETAILED DESCRIPTION

Figure 1:
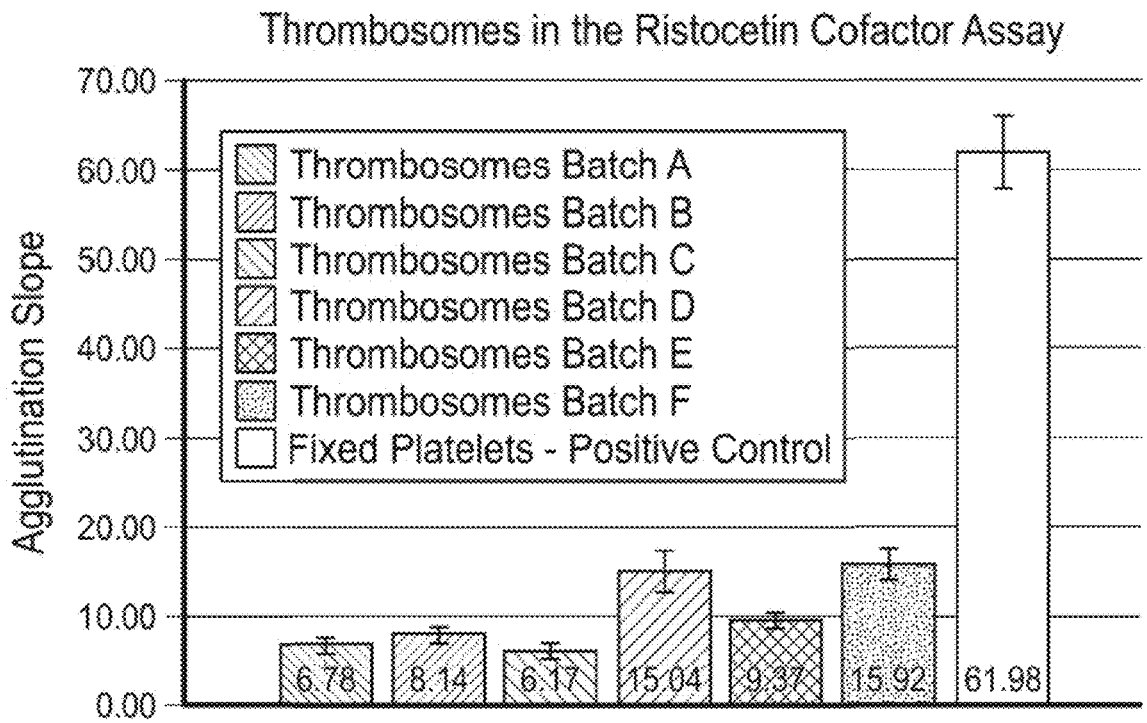
FIG. 1 is a graph showing aggregation slope of six separate lots of thrombosomes (A-F) compared to formalin-fixed platelets (positive control) in a ristocetin aggregation assay. Ristocetin failed to aggregate thrombosomes and all thrombosomes lots (A-F) were significantly different from the fixed platelet positive control.

This disclosure is directed to compositions and methods for use of platelets, platelet derivatives, or thrombosomes as biological carriers of cargo, such as anti-fibrinolytic compounds, also referred to herein as anti-fibrinolytic loaded platelets, platelet derivatives, or thrombosomes. This disclosure is also directed to compositions and methods for use of unloaded platelets, platelet derivatives, or thrombosomes in the treatment of a disease such as von Willebrand disease, or conditions such as hemorrhaging or trauma.

Anti-fibrinolytic loaded platelets described herein can be stored under typical ambient conditions, refrigerated, cryopreserved, for example with dimethyl sulfoxide (DMSO), and/or lyophilized after stabilization (e.g., to form thrombosomes).

It is to be understood that the terminology used herein is for the purpose of describing particular embodiments only, and is not intended to be limiting. Further, where a range of values is disclosed, the skilled artisan will understand that all other specific values within the disclosed range are inherently disclosed by these values and the ranges they represent without the need to disclose each specific value or range herein. For example, a disclosed range of 1-10 includes 1-9, 1-5, 2-10, 3.1-6, 1, 2, 3, 4, 5, and so forth. In addition, each disclosed range includes up to 5% lower for the lower value of the range and up to 5% higher for the higher value of the range. For example, a disclosed range of 4-10 includes 3.8-10.5. This concept is captured in this document by the term "about".

As used herein and in the appended claims, the singular forms "a", "an", and "the" include plural referents unless the context clearly dictates otherwise. Thus, for example, reference to "a platelet" includes a plurality of such platelets. Furthermore, the use of terms that can be described using equivalent terms include the use of those equivalent terms. Thus, for example, the use of the term "subject" is to be understood to include the terms "patient", "individual," or "animal" and other terms used in the art to indicate one who is subject to a treatment.

As used herein, and unless otherwise specified, the terms "treat," "treating" and "treatment" contemplate an action that occurs while a subject is suffering from a disease (e.g., von Willebrand disease), disorder, and/or condition (e.g., hemorrhage) which reduces the severity of the disease, disorder, and/or conditions or slows the progression of the disease, disorder, or condition ("therapeutic treatment"), and which can inhibit the disease, disorder, and/or condition (e.g., hemorrhage).

As used herein, and unless otherwise specified, a "therapeutically effective amount" of is an amount sufficient to provide a therapeutic benefit in the treatment of the disease, disorder and/or condition (e.g., hemorrhage) or to delay or minimize one or more symptoms associated with the disease, disorder, and/or condition. A therapeutically effective amount means an amount of therapeutic agent, alone or in combination with other therapies, which provides a therapeutic benefit in the treatment of the disease, disorder, and/or condition. The term "therapeutically effective amount" can encompass an amount that improves overall therapy, reduces or avoids symptoms or causes of the disease, disorder and/or condition, or enhances the therapeutic efficacy of another therapeutic agent.

Unless defined otherwise, all technical and scientific terms used herein have the same meaning as commonly understood by one of ordinary skill in the art to which the term belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the term "platelet" can include whole platelets, fragmented platelets, platelet derivatives, or thrombosomes. "Platelets" within the above definition may include, for example, platelets in whole blood, platelets in plasma, platelets in buffer optionally supplemented with select plasma proteins, cold stored platelets, dried platelets, cryopreserved platelets, thawed cryopreserved platelets, rehydrated dried platelets, rehydrated cryopreserved platelets, lyopreserved platelets, thawed cryopreserved platelets, or rehydrated lyopreserved platelets. "Platelets" may be "platelets" of mammals, such as of humans, or such as of non-human mammals.

Thus, for example, reference to "anti-fibrinolytic loaded platelets" may be inclusive of anti-fibrinolytic loaded platelets as well as anti-fibrinolytic loaded platelet derivatives or anti-fibrinolytic loaded thrombosomes, unless the context clearly dictates a particular form.

As used herein, "thrombosomes" (sometimes also herein called "Tsomes" or "Ts", particularly in the Examples and Figures) are platelet derivatives that have been treated with an incubating agent (e.g., any of the incubating agents described herein) and lyopreserved (e.g., freeze-dried to form thrombosomes). In some cases, thrombosomes can be prepared from pooled platelets. Thrombosomes can have a shelf life of 2-3 years in dry form at ambient temperature and can be rehydrated with sterile water within minutes for immediate infusion.

As used herein and in the appended claims, the term "fresh platelet" includes platelets stored for less than approximately 24 hours.

As used herein and in the appended claims the term "stored platelet" includes platelets stored for approximately 24 hours or longer before use.

As used herein and in the appended claims the term "fixed platelet" includes platelets fixed with a formalin solution.

As used herein and in the appended claims the term "unloaded" includes platelets, platelet derivatives, and/or thrombosomes that are not loaded with an active agent, such as platelets, platelet derivatives, and/or thrombosomes that are not loaded with an anti-fibrinolytic.

In some embodiments, rehydrating the anti-fibrinolytic loaded platelets includes adding to the platelets an aqueous liquid. In some embodiments, the aqueous liquid is water. In some embodiments, the aqueous liquid is an aqueous solution. In some embodiments, the aqueous liquid is a saline solution. In some embodiments, the aqueous liquid is a suspension.

In some embodiments, the rehydrated platelets have coagulation factor levels showing all individual factors (e.g., Factors VII, VIII and IX) associated with blood clotting at 40 international units (IU) or greater.

As used herein, "coagulopathy" is a bleeding disorder in which the blood's ability to coagulate (e.g., form clots) is impaired. This condition can cause a tendency toward prolonged or excessive bleeding (e.g., diathesis). In some embodiments, a coagulopathy is caused by a disease (e.g., Von Willebrand disease). In some embodiments, a coagulopathy is a drug induced coagulopathy. In some embodiments, a coagulopathy is induced by an antiplatelet agent-induced coagulopathy. In some embodiments, a coagulopathy is induced by an anti-platelet agent.

In some embodiments, the dried platelets, such as freeze-dried platelets, have less than about 10%, such as less than about 8%, such as less than about 6%, such as less than about 4%, such as less than about 2%, such as less than about 0.5% crosslinking of platelet membranes via proteins and/or lipids present on the membranes. In some embodiments, the dried platelets, such as freeze dried platelets, have less than about 10%, such as less than about 8%, such as less than about 6%, such as less than about 4%, such as less than about 2%, such as less than about 0.5% crosslinking of platelet membranes via proteins and/or lipids present on the membranes. In some embodiments, the rehydrated platelets, have less than about 10%, such as less than about 8%, such as less than about 6%, such as less than about 4%, such as less than about 2%, such as less than about 0.5% crosslinking of platelet membranes via proteins and/or lipids present on the membranes. In some embodiments, the rehydrated platelets, have between about 0.01% to about 5%, such as between about 0.1% to about 4%, such as between about 1% to between about 3%, such as between about 1% to about 2%, crosslinking of platelet membranes via proteins and/or lipids present on the membranes. In some embodiments, the rehydrated platelets, have at least about 1% to at least about 10, such as less than about 8%, such as less than about 6%, such as less than about 4%, such as less than about 2%, such as less than about 0.5% crosslinking of platelet membranes via proteins and/or lipids present on the membranes.

In some embodiments, the anti-fibrinolytic loaded platelets and the dried platelets, such as freeze-dried platelets, having a particle size (e.g., diameter, max dimension) of at least about 0.2 μm (e.g., at least about 0.3 μm, at least about 0.4 μm, at least about 0.5 μm, at least about 0.6 μm, at least about 0.7 μm, at least about 0.8 μm, at least about 0.9 μm, at least about 1.0 μm, at least about 1.0 μm, at least about 1.5 μm, at least about 2.0 μm, at least about 2.5 μm, or at least about 5.0 μm). In some embodiments, the particle size is less than about 5.0 μm (e.g., less than about 2.5 μm, less than about 2.0 μm, less than about 1.5 μm, less than about 1.0 μm, less than about 0.9 μm, less than about 0.8 μm, less than about 0.7 μm, less than about 0.6 μm, less than about 0.5 μm, less than about 0.4 μm, or less than about 0.3 μm). In some embodiments, the particle size is from about 0.3 μm to about 5.0 μm (e.g., from about 0.4 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm).

In some embodiments, at least 50% (e.g., at least about 55%, at least about 60%, at least about 65%, at least about 70%, at least about 75%, at least about 80%, at least about 85%, at least about 90%, at least about 95%, or at least about 99%) of platelets and/or the dried platelets, such as freeze-dried platelets, have a particle size in the range of about 0.3 μm to about 5.0 μm (e.g., from about 0.4 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm). In some embodiments, at most 99% (e.g., at most about 95%, at most about 80%, at most about 75%, at most about 70%, at most about 65%, at most about 60%, at most about 55%, or at most about 50%) of platelets and/or the dried platelets, such as freeze-dried platelets, are in the range of about 0.3 μm to about 5.0 μm (e.g., from about 0.4 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm). In some embodiments, about 50% to about 99% (e.g., about 55% to about 95%, about 60% to about 90%, about 65% to about 85, about 70% to about 80%) of platelets and/or the dried platelets, such as freeze-dried platelets, are in the range of about 0.3 μm to about 5.0 μm (e.g., from about 0.4 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm).

In some embodiments, (e.g., using unloaded platelets or platelet derivatives), the platelets or platelet derivatives are prepared consistent with the procedures described in U.S.

Pat. No. 8,486,617 (such as, e.g., Examples 1-5) and U.S. Pat. No. 8,097,403 (such as, e.g., Examples 1-3).

Also provided herein are methods of preparing anti-fibrinolytic loaded platelets. In some embodiments, platelets are isolated prior to contacting the platelets with an anti-fibrinolytic.

Accordingly, in some embodiments, the methods for preparing anti-fibrinolytic loaded platelets includes: step (a) isolating platelets, for example in a liquid medium; and step (b) contacting the platelets with an anti-fibrinolytic, and with a loading buffer comprising a salt, a base, a loading agent, and optionally ethanol, to form the anti-fibrinolytic loaded platelets.

Accordingly, in some embodiments, the methods for preparing anti-fibrinolytic loaded platelets includes: step (a) isolating platelets, for example in a liquid medium; step (b) contacting the platelets with an anti-fibrinolytic to form a first composition; and step (c) contacting the first composition with a buffer comprising a salt, a base, a loading agent, and optionally at least one organic solvent to form the anti-fibrinolytic loaded platelets.

In some embodiments, suitable organic solvents include, but are not limited to alcohols, esters, ketones, ethers, halogenated solvents, hydrocarbons, nitriles, glycols, alkyl nitrates, water or mixtures thereof. In some embodiments, suitable organic solvents includes, but are not limited to methanol, ethanol, n-propanol, isopropanol, acetic acid, acetone, methyl ethyl ketone, methyl isobutyl ketone, methyl acetate, ethyl acetate, isopropyl acetate, tetrahydrofuran, isopropyl ether (IPE), tert-butyl methyl ether, dioxane (e.g., 1,4-dioxane), acetonitrile, propionitrile, methylene chloride, chloroform, toluene, anisole, cyclohexane, hexane, heptane, ethylene glycol, nitromethane, dimethylformamide, dimethyl sulfoxide, N-methyl pyrrolidone, dimethylacetamide, and combinations thereof.

Accordingly, in some embodiments, the methods for preparing anti-fibrinolytic loaded platelets includes: step (a) isolating platelets, for example in a liquid medium; step (b) contacting the platelets with a buffer comprising a salt, a base, a loading agent, and optionally at least one organic solvent, to form a first composition; and step (c) contacting the first composition with an anti-fibrinolytic, to form the anti-fibrinolytic loaded platelets.

In some embodiments, isolating platelets includes isolating platelets from blood.

In some embodiments, platelets are donor-derived platelets. In some embodiments, platelets are obtained by a process that includes an apheresis step. In some embodiments, platelets are fresh platelets. In some embodiments, platelets are stored platelets.

In some embodiments, platelets are derived in vitro. In some embodiments, platelets are derived or prepared in a culture prior to contacting the platelets with an anti-fibrinolytic. In some embodiments, preparing the platelets includes deriving or growing the platelets from a culture of megakaryocytes. In some embodiments, preparing the platelets includes deriving or growing the platelets (or megakaryocytes) from a culture of human pluripotent stem cells (PCSs), including embryonic stem cells (ESCs) and/or induced pluripotent stem cells (iPSCs).

In some embodiments, the loading agent is a saccharide. In some embodiments, the saccharide is a monosaccharide. In some embodiments, the saccharide is a disaccharide. In some embodiments, the saccharide is a non-reducing disaccharide. In some embodiments, the saccharide is sucrose, maltose, trehalose, glucose (e.g., dextrose), mannose, or xylose. In some embodiments, the loading agent is a starch.

In some embodiments, a loading agent is a cryoprotectant. In some embodiments, (e.g., for platelets or platelet derivatives not loaded with an anti-fibrinolytic agent), a "loading agent" can be used in the preparation of the platelets or platelet derivatives, for example, as part of an incubating agent.

As used herein, the term "anti-fibrinolytic," "anti-fibrinolytics," or "anti-fibrinolytic compound," is any compound capable of inhibiting fibrinolysis. Fibrinolysis is the process where the activated plasminogen removes excess fibrin and promotes fibrin clot formation and wound healing (Szekely, A. and Lex, D. J., Antifibrinolytics, *Heart Lung Vessel*, 6(1): 5-7, (2014), which is incorporated herein by reference in its entirety). Inhibiting fibrinolysis can be useful under certain conditions. For example, in the case of traumatic bleeding events and/or hemorrhage, inhibiting fibrinolysis can enhance the formation of blood clots (e.g., stopping bleeding).

In some embodiments, the anti-fibrinolytic can be ε-aminocaproic acid. In some embodiments, the anti-fibrinolytic can be tranexamic acid. In some embodiments, the anti-fibrinolytic can be aprotinin. In some embodiments, the anti-fibrinolytic can be aminomethylbenzoic acid. In some embodiments, the anti-fibrinolytic can be fibrinogen. In some embodiments, the anti-fibrinolytic can be a combination of two or more anti-fibrinolytics.

Provided herein are methods to treat acquired von Willebrand disease (e.g., any of the von Willebrand diseases described herein), comprising a therapeutically effective amount of unloaded thrombosomes, wherein the unloaded thrombosomes are prepared by a process comprising contacting thrombosomes with a loading buffer including a salt, a base, a loading agent, and optionally at least one organic solvent, and a step of freeze-drying, to form the unloaded thrombosomes.

Provided herein are methods to treat von Willebrand disease, comprising a therapeutically effective amount of unloaded thrombosomes prepared by a process comprising providing platelets and contacting the platelets with a loading buffer including a salt, a base, a loading agent, and optionally at least one organic solvent, and a step of freeze-drying, to form the unloaded thrombosomes.

Provided herein are methods to treat von Willebrand disease, comprising a therapeutically effective amount of unloaded thrombosomes, wherein the unloaded thrombosomes are prepared by a process comprising contacting platelets with a loading buffer including a salt and a base to form a first composition and contacting the first composition with a loading agent, and optionally at least one organic solvent, and a step of freeze-drying, to form the unloaded thrombosomes.

Provided herein are methods to treat von Willebrand disease, comprising a therapeutically effective amount of unloaded thrombosomes, wherein the unloaded thrombosomes are prepared by a process comprising contacting platelets with a loading agent, and optionally at least one organic solvent to form a first composition and contacting the first composition with a loading buffer including a salt and a base, and a freeze-drying step, to form the unloaded thrombosomes.

Provided herein are methods to treat von Willebrand disease, comprising a therapeutically effective amount of unloaded thrombosomes, wherein the unloaded thrombosomes are prepared by a process comprising contacting platelets a loading buffer including a salt, a base, a loading agent, and optionally at least one organic solvent, and a step of freeze-drying to form the anti-fibrinolytic-loaded thrombosomes. In some embodiments of preparing unloaded thrombosomes, the platelets are pooled from a plurality of donors prior to a treating step.

Provided herein are methods to treat von Willebrand disease, comprising a therapeutically effective amount of unloaded thrombosomes, wherein the unloaded thrombosomes are prepared by a process comprising A) pooling platelets from a plurality of donors and B) contacting the platelets from step (A) with a loading buffer including a salt, a base, a loading agent, and optionally at least one organic solvent, and a freeze-drying step, to form the unloaded thrombosomes.

Provided herein are methods to treat von Willebrand disease, comprising a therapeutically effective amount of unloaded thrombosomes, wherein the unloaded thrombosomes are prepared by a process comprising A) pooling platelets from a plurality of donors and B) contacting the platelets from step (A) with a loading buffer including a salt and a base to form a first composition and contacting the first composition with a loading agent, and optionally at least one organic solvent, and a step of freeze-drying, to form the unloaded thrombosomes.

Provided herein are methods to treat von Willebrand disease, comprising a therapeutically effective amount of unloaded thrombosomes, wherein the unloaded thrombosomes are prepared by a process comprising A) pooling platelets from a plurality of donors and B) contacting the platelets from step (A) with an a loading agent to form a first composition and contacting the first composition with a loading buffer including a salt and a base, and optionally at least one organic solvent, and a step of freeze-drying, to form the unloaded thrombosomes.

In some embodiments, no solvent is used. Thus, provided herein are methods to treat von Willebrand disease, comprising a therapeutically effective amount of unloaded thrombosomes, wherein the unloaded thrombosomes are prepared by a process comprising:
  A) isolating platelets, for example in a liquid medium;
  B) contacting the platelets with an unloaded and with a loading buffer comprising a salt, a base, and a loading agent, to form the unloaded platelets,
    wherein the method does not comprise contacting the platelets with an organic solvent such as ethanol, and
  C) a step of freeze-drying, to form the unloaded thrombosomes.

Provided herein are methods to treat von Willebrand disease, comprising a therapeutically effective amount of unloaded thrombosomes, wherein the unloaded thrombosomes are prepared by a process comprising:
  A) isolating platelets, for example in a liquid medium;
  B) contacting the platelets with an unloaded to form a first composition;
  C) contacting the first composition with a buffer comprising a salt, a base, and a loading agent, to form the unloaded platelets,
    wherein the method does not comprise contacting the platelets with an organic solvent such as ethanol and the method does not comprise contacting the first composition with an organic solvent such as ethanol, and
  (D) a step freeze-drying, to form the unloaded thrombosomes.

Provided herein are methods to treat von Willebrand disease, comprising a therapeutically effective amount of unloaded thrombosomes, wherein the unloaded thrombosomes are prepared by a process comprising:
  A) isolating platelets, for example in a liquid medium;
  B) contacting the platelets with a buffer comprising a salt and a base, to form a first composition;
  C) contacting the first composition with a loading agent, to form the unloaded platelets,
    wherein the method does not comprise contacting the platelets with an organic solvent such as ethanol and the method does not comprise contacting the first composition with an organic solvent such as ethanol and
  D) a step of freeze drying, to form the unloaded thrombosomes.

Provided herein are methods to treat von Willebrand disease, comprising a therapeutically effective amount of unloaded thrombosomes, wherein the unloaded thrombosomes are prepared by a process comprising:
  A) preparing platelets;
  B) contacting the platelets with an anti-fibrinolytic and with a loading buffer comprising a salt, a base, and a loading agent, to form the unloaded platelets,
    wherein the method does not comprise contacting the platelets with an organic solvent such as ethanol, and
  C) a step of freeze-drying, to form the unloaded thrombosomes.

Provided herein are methods to treat von Willebrand disease, comprising a therapeutically effective amount of unloaded thrombosomes, wherein the unloaded thrombosomes are prepared by a process comprising:
  a) preparing platelets;
  b) contacting the platelets with a loading agent to form a first composition;
  c) contacting the first composition with a buffer comprising a salt and a base, to form the unloaded platelets,
    wherein the method does not comprise contacting the platelets with an organic solvent such as ethanol and the method does not comprise contacting the first composition with an organic solvent such as ethanol and
  d) a step of freeze-drying, to form the unloaded thrombosomes.

Provided herein are methods to treat von Willebrand disease (e.g., any of the von Willebrand diseases described herein), comprising a therapeutically effective amount of anti-fibrinolytic loaded thrombosomes, wherein the anti-fibrinolytic loaded thrombosomes are prepared by a process comprising contacting thrombosomes with an anti-fibrinolytic and with a loading buffer including a salt, a base, a loading agent, and optionally at least one organic solvent, and a step of freeze-drying, to form the anti-fibrinolytic loaded thrombosomes.

Provided herein are methods to treat von Willebrand disease (e.g., any of the von Willebrand diseases described herein), comprising a therapeutically effective amount of anti-fibrinolytic loaded thrombosomes prepared by a process comprising providing platelets and contacting the platelets with an anti-fibrinolytic and with a loading buffer including a salt, a base, a loading agent, and optionally at least one organic solvent, and a step of freeze-drying, to form the anti-fibrinolytic loaded thrombosomes. In some embodiments of preparing anti-fibrinolytic loaded platelets, the platelets are contacted with the anti-fibrinolytic and with the loading buffer sequentially, in either order.

Provided herein are methods to treat von Willebrand disease (e.g., any of the von Willebrand diseases described herein), comprising a therapeutically effective amount of anti-fibrinolytic loaded thrombosomes, wherein the anti-fibrinolytic loaded thrombosomes are prepared by a process comprising contacting platelets with the anti-fibrinolytic to form a first composition and contacting the first composition with a loading buffer including a salt, a base, a loading agent, and optionally at least one organic solvent, and a step of freeze-drying, to form the anti-fibrinolytic loaded thrombosomes.

Provided herein are methods to treat von Willebrand disease (e.g., any of the von Willebrand diseases described herein), comprising a therapeutically effective amount of anti-fibrinolytic loaded thrombosomes, wherein the anti-fibrinolytic loaded thrombosomes are prepared by a process comprising contacting platelets with a buffer including a salt, a base, a loading agent, and optionally at least one organic solvent to form a first composition and contacting the first composition with an anti-fibrinolytic, and a freeze drying step, to form the anti-fibrinolytic loaded thrombosomes. In some embodiments of preparing anti-fibrinolytic loaded thrombosomes, the platelets are contacted with the anti-fibrinolytic and with the loading buffer concurrently.

Provided herein are methods to treat von Willebrand disease (e.g., any of the von Willebrand diseases described herein), comprising a therapeutically effective amount of anti-fibrinolytic loaded thrombosomes, wherein the anti-fibrinolytic loaded thrombosomes are prepared by a process comprising contacting platelets with an anti-fibrinolytic in the presence of a loading buffer including a salt, a base, a loading agent, and optionally at least one organic solvent, and a step of freeze-drying to form the anti-fibrinolytic-loaded thrombosomes. In some embodiments of preparing anti-fibrinolytic loaded thrombosomes, the platelets are pooled from a plurality of donors prior to a treating step.

Provided herein are methods to treat von Willebrand disease (e.g., any of the von Willebrand diseases described herein), comprising a therapeutically effective amount of anti-fibrinolytic loaded thrombosomes, wherein the anti-fibrinolytic loaded thrombosomes are prepared by a process comprising A) pooling platelets from a plurality of donors and B) contacting the platelets from step (A) with an anti-fibrinolytic and with a loading buffer including a salt, a base, a loading agent, and optionally at least one organic solvent, and a freeze-drying step, to form the anti-fibrinolytic loaded thrombosomes.

Provided herein are methods to treat von Willebrand disease (e.g., any of the von Willebrand diseases described herein), comprising a therapeutically effective amount of anti-fibrinolytic loaded thrombosomes, wherein the anti-fibrinolytic loaded thrombosomes are prepared by a process comprising A) pooling platelets from a plurality of donors and B) contacting the platelets from step (A) with an anti-fibrinolytic to form a first composition and contacting the first composition with a loading buffer including a salt, a base, a loading agent, and optionally at least one organic solvent, and a step of freeze-drying, to form the anti-fibrinolytic loaded thrombosomes.

Provided herein are methods to treat von Willebrand disease (e.g., any of the von Willebrand diseases described herein), comprising a therapeutically effective amount of anti-fibrinolytic loaded thrombosomes, wherein the anti-fibrinolytic loaded thrombosomes are prepared by a process comprising A) pooling platelets from a plurality of donors and B) contacting the platelets from step (A) with an anti-fibrinolytic to form a first composition and contacting the first composition with a loading buffer including a salt, a base, a loading agent, and optionally at least one organic solvent, and a step of freeze-drying, to form the anti-fibrinolytic loaded thrombosomes.

Provided herein are methods to treat von Willebrand disease (e.g., any of the von Willebrand diseases described herein), comprising a therapeutically effective amount of anti-fibrinolytic loaded thrombosomes, wherein the anti-fibrinolytic loaded thrombosomes are prepared by a process comprising A) pooling platelets from a plurality of donors and B) contacting the platelets from step (A) with a loading buffer including a salt, a base, a loading agent, and optionally at least one organic solvent, to form a first composition and contacting the first composition with an anti-fibrinolytic, and a step of freeze-drying to form the anti-fibrinolytic loaded thrombosomes.

Provided herein are methods to treat von Willebrand disease (e.g., any of the von Willebrand diseases described herein), comprising a therapeutically effective amount of anti-fibrinolytic loaded thrombosomes, wherein the anti-fibrinolytic loaded thrombosomes are prepared by a process comprising A) pooling platelets from a plurality of donors and B) contacting the platelets with an anti-fibrinolytic in the presence of a loading buffer including a salt, a base, a loading agent, and optionally at least one organic solvent, and a step of freeze-drying, to form the anti-fibrinolytic loaded thrombosomes.

In some embodiments, no solvent is used. Thus, provided herein are methods to treat von Willebrand disease, comprising a therapeutically effective amount of anti-fibrinolytic loaded thrombosomes, wherein the anti-fibrinolytic thrombosomes are prepared by a process comprising:
  A) isolating platelets, for example in a liquid medium;
  D) contacting the platelets with an anti-fibrinolytic and with a loading buffer comprising a salt, a base, and a loading agent, to form the anti-fibrinolytic loaded platelets,
  wherein the method does not comprise contacting the platelets with an organic solvent such as ethanol, and
  C) a step of freeze-drying, to form the anti-fibrinolytic loaded thrombosomes.

Provided herein are methods to treat von Willebrand disease, comprising a therapeutically effective amount of anti-fibrinolytic loaded thrombosomes, wherein the anti-fibrinolytic thrombosomes are prepared by a process comprising:
  A) isolating platelets, for example in a liquid medium;
  B) contacting the platelets with an anti-fibrinolytic to form a first composition;
  E) contacting the first composition with a buffer comprising a salt, a base, and a loading agent, to form the anti-fibrinolytic loaded platelets,
  wherein the method does not comprise contacting the platelets with an organic solvent such as ethanol and the method does not comprise contacting the first composition with an organic solvent such as ethanol, and
  (D) a step freeze-drying, to form the anti-fibrinolytic loaded thrombosomes.

Provided herein are methods to treat von Willebrand disease, comprising a therapeutically effective amount of anti-fibrinolytic loaded thrombosomes, wherein the anti-fibrinolytic thrombosomes are prepared by a process comprising:
  A) isolating platelets, for example in a liquid medium;
  B) contacting the platelets with a buffer comprising a salt, a base, and a loading agent, to form a first composition;
  C) contacting the first composition with an anti-fibrinolytic, to form the anti-fibrinolytic loaded platelets,
  wherein the method does not comprise contacting the platelets with an organic solvent such as ethanol and the method does not comprise contacting the first composition with an organic solvent such as ethanol and
  D) a step of freeze drying, to form the anti-fibrinolytic loaded thrombosomes.

Provided herein are methods to treat von Willebrand disease, comprising a therapeutically effective amount of anti-fibrinolytic loaded thrombosomes, wherein the anti-fibrinolytic thrombosomes are prepared by a process comprising:
- A) preparing platelets;
- D) contacting the platelets with an anti-fibrinolytic and with a loading buffer comprising a salt, a base, and a loading agent, to form the anti-fibrinolytic loaded platelets,
  wherein the method does not comprise contacting the platelets with an organic solvent such as ethanol, and
- E) a step of freeze-drying, to form the anti-fibrinolytic loaded thrombosomes.

Provided herein are methods to treat von Willebrand disease, comprising a therapeutically effective amount of anti-fibrinolytic loaded thrombosomes, wherein the anti-fibrinolytic thrombosomes are prepared by a process comprising:
- a) preparing platelets;
- b) contacting the platelets with an anti-fibrinolytic to form a first composition;
- c) contacting the first composition with a buffer comprising a salt, a base, and a loading agent, to form the anti-fibrinolytic loaded platelets,
  wherein the method does not comprise contacting the platelets with an organic solvent such as ethanol and the method does not comprise contacting the first composition with an organic solvent such as ethanol and
- d) a step of freeze-drying, to form the anti-fibrinolytic loaded thrombosomes.

Provided herein are methods to treat von Willebrand disease, comprising a therapeutically effective amount of anti-fibrinolytic loaded thrombosomes, wherein the anti-fibrinolytic thrombosomes are prepared by a process comprising:
- a) preparing platelets;
- b) contacting the platelets with a buffer comprising a salt, a base, and a loading agent, to form a first composition;
- c) contacting the first composition with an anti-fibrinolytic, to form the anti-fibrinolytic loaded platelets.
  wherein the method does not comprise contacting the platelets with an organic solvent such as ethanol and the method does not comprise contacting the first composition with an organic solvent such as ethanol and
- d) a freeze-drying step, to form the anti-fibrinolytic loaded thrombosomes.

In some embodiments, an anti-fibrinolytic (e.g., EACA) loaded into platelets is modified to include an imaging agent. For example, an anti-fibrinolytic can be modified with an imaging agent in order to image the anti-fibrinolytic loaded platelet in vivo. In some embodiments, an anti-fibrinolytic can be modified with two or more imaging agents (e.g., any two or more of the imaging agents described herein). In some embodiments, an anti-fibrinolytic loaded into platelets is modified with a radioactive metal ion, a paramagnetic metal ion, a gamma-emitting radioactive halogen, a positron-emitting radioactive non-metal, a hyperpolarized NMR-active nucleus, a reporter suitable for in vivo optical imaging, or a beta-emitter suitable for intravascular detection. For example, a radioactive metal ion can include, but is not limited to, positron emitters such as $^{54}$Cu, $^{48}$V, $^{52}$Fe, $^{55}$Co, $^{94}$Tc or $^{68}$Ga; or gamma-emitters such as $^{171}$Tc, $^{111}$In, $^{113}$In, or $^{67}$Ga. For example, a paramagnetic metal ion can include, but is not limited to Gd(III), a Mn(II), a Cu(II), a Cr(III), a Fe(III), a Co(II), a Er(II), a Ni(II), a Eu(III) or a Dy(III), an element comprising an Fe element, a neodymium iron oxide (NdFeO3) or a dysprosium iron oxide (DyFeO3). For example, a paramagnetic metal ion can be chelated to a polypeptide or a monocrystalline nanoparticle. For example, a gamma-emitting radioactive halogen can include, but is not limited to $^{123}$I, $^{131}$I or $^{77}$Br. For example, a positron-emitting radioactive non-metal can include, but is not limited to $^{11}$C, $^{13}$N, $^{15}$O, $^{17}$F, $^{18}$F, $^{75}$Br, $^{76}$Br or $^{124}$I. For example, a hyperpolarized NMR-active nucleus can include, but is not limited to $^{13}$C, $^{15}$N, $^{19}$F, $^{29}$Si and $^{31}$P. For example, a reporter suitable for in vivo optical imaging can include, but is not limited to any moiety capable of detection either directly or indirectly in an optical imaging procedure. For example, the reporter suitable for in vivo optical imaging can be a light scatterer (e.g., a colored or uncolored particle), a light absorber or a light emitter. For example, the reporter can be any reporter that interacts with light in the electromagnetic spectrum with wavelengths from the ultraviolet to the near infrared. For example, organic chromophoric and fluorophoric reporters include groups having an extensive delocalized electron system, e.g. cyanines, merocyanines, indocyanines, phthalocyanines, naphthalocyanines, triphenylmethanes, porphyrins, pyrylium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, b/s(dithiolene) complexes, bis(benzene-dithiolate) complexes, iodoaniline dyes, b/stS.O-dithiolene) complexes. For example, the reporter can be, but is not limited to a fluorescent, a bioluminescent, or chemiluminescent polypeptide. For example, a fluorescent or chemiluminescent polypeptide is a green florescent protein (GFP), a modified GFP to have different absorption/emission properties, a luciferase, an aequorin, an obelin, a mnemiopsin, a berovin, or a phenanthridinium ester. For example, a reporter can be, but is not limited to rare earth metals (e.g., europium, samarium, terbium, or dysprosium), or fluorescent nanocrystals (e.g., quantum dots). For example, a reporter may be a chromophore that can include, but is not limited to fluorescein, sulforhodamine 101 (Texas Red), rhodamine B, rhodamine 6G, rhodamine 19, indocyanine green, Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750. For example, a beta-emitter can include, but is not limited to radio metals $^{67}$Cu, $^{89}$Sr, $^{90}$Y, $^{153}$Sm, $^{185}$Re, $^{188}$Re or $^{192}$Ir, and non-metals $^{32}$P, $^{33}$P, $^{38}$S, $^{38}$Cl, $^{39}$Cl, $^{82}$Br and $^{83}$Br. In some embodiments, an anti-fibrinolytic loaded into platelets can be associated with gold or other equivalent metal particles (such as nanoparticles). For example, a metal particle system can include, but is not limited to gold nanoparticles (e.g., Nanogold™).

In some embodiments, an anti-fibrinolytic loaded into platelets that is modified with an imaging agent is imaged using an imaging unit. The imaging unit can be configured to image the anti-fibrinolytic loaded platelets in vivo based on an expected property (e.g., optical property from the imaging agent) to be characterized. For example, imaging techniques (in vivo imaging using an imaging unit) that can be used, but are not limited to are: computer assisted tomography (CAT), magnetic resonance spectroscopy (MRS), magnetic resonance imaging (MRI), positron emission tomography (PET), single-photon emission computed tomography (SPECT), or bioluminescence imaging (BLI). Chen, Z., et al., Advance of Molecular Imaging Technology and Targeted Imaging Agent in Imaging and Therapy, *Biomed Res Int.*, 819324, doi: 10.1155/2014/819324 (2014) have described various imaging techniques and which is incorporated by reference herein in its entirety.

In some embodiments, the platelets are isolated prior to a contacting step. In some embodiments, the methods further include isolating platelets by using centrifugation. In some embodiments, the centrifugation occurs at a relative centrifugal force (RCF) of about 800 g to about 2000 g. In some embodiments, the centrifugation occurs at relative centrifugal force (RCF) of about 1300 g to about 1800 g. In some embodiments, the centrifugation occurs at relative centrifugal force (RCF) of about 1500 g. In some embodiments, the centrifugation occurs for about 1 minute to about 60 minutes. In some embodiments, the centrifugation occurs for about 10 minutes to about 30 minutes. In some embodiments, the centrifugation occurs for about 20 minutes.

In some embodiments, the platelets are at a concentration from about 1,000 platelets/µl to about 10,000,000 platelets/µl. In some embodiments, the platelets are at a concentration from about 50,000 platelets/µl to about 4,000,000 platelets/µl. In some embodiments, the platelets are at a concentration from about 100,000 platelets/µl to about 300,000,000 platelets/µl. In some embodiments, the platelets are at a concentration from about 1,000,000 to about 2,000,000. In some embodiments, the platelets are at a concentration of about 2,000,000 platelets/µl.

In some embodiments, the platelets are at a concentration from about 1,000 platelets to about 10,000,000 platelets. In some embodiments, the platelets are at a concentration from about 50,000 platelets to about 4,000,000 platelets. In some embodiments, the platelets are at a concentration from about 100,000 platelets to about 300,000,000 platelets. In some embodiments, the platelets are at a concentration from about 1,000,000 to about 2,000,000. In some embodiments, the platelets are at a concentration of about 2,000,000 platelets.

Unloaded platelets can be used, for example, in therapeutic applications as disclosed herein. For example, unloaded platelets, unloaded platelet derivatives, and/or unloaded thrombosomes can be used to treat a disease, such as von Willebrand disease. In some embodiments, unloaded platelets, unloaded platelet derivatives, and/or unloaded thrombosomes can be used to treat von Willebrand disease. In some embodiments, unloaded platelets, unloaded platelet derivatives, and/or unloaded thrombosomes can be used to treat in a non-limiting way von Willebrand disease type 1, von Willebrand disease type 2, or von Willebrand disease type 3. In some embodiments, unloaded platelets, unloaded platelet derivatives, and/or unloaded thrombosomes can be used to treat acquired von Willebrand disease. Generally, acquired von Willebrand disease occurs with an autoimmune disorder (e.g., lupus) or after taking certain medications.

Von Willebrand disease is a congenital coagulation disorder caused by the lack or a defect in the gene required to produce active von Willebrand protein (e.g., von Willebrand factor (vWF). The disease affects about 1% of the population. Von Willebrand disease manifests itself with patients experiencing frequent nosebleeds, easy bruising, excessive bleeding during menstruation, and/or invasive procedures. vWF is produced in endothelial cells and megakaryocytes and is released into circulation bound to Factor VIII. Von Willebrand factor assists during platelet plug formation by binding both clotting factor VIII and platelets. The plasma levels of vWF in a human subject are about 1 ug/mL with a half-life of about two hours. vWF under shear vascular stress binds to exposed collagen of damaged vascular subendothelium. vWF binding to the subendothelium collagen bridges platelets binding to the site of injury. The vWF binds platelets through the GPIbα receptor (CD42b) and the GPIIb-IIIα receptor (CD41/CD61) complex. A subject lacking functioning vWF protein lack and/or have a reduced ability to clot blood easily, and therefore bleed readily upon injury. In some embodiments, thrombosomes can function as a stabilized platelet product and can participate in clot formation. In some embodiments, thrombosomes can participate in clot formation in the absence of vWF. In some embodiments, bound thrombosomes can help potentiate thrombin production and strengthen a blood clot.

In some embodiments, the surface expression of CD42b on the therapeutically effective amount of unloaded thrombosomes is about 50% less than the surface expression of CD42b on platelets. In some embodiments, the surface expression of CD42b on the therapeutically effective amount of unloaded thrombosomes is about 40% less than the surface expression of CD42b on platelets. In some embodiments, the surface expression of CD42b on the therapeutically effective amount of unloaded thrombosomes is about 25% less than the surface expression of CD42b on platelets. In some embodiments, the surface expression of CD42b on the therapeutically effect amount of unloaded thrombosomes is about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, or about 25%.

In some embodiments, the therapeutically effective amount of unloaded thrombosomes forms clots at about 60% of the time platelets form clots. In some embodiments, the therapeutically effective amount of unloaded thrombosomes forms clots at about 70% of the time platelets form clots. In some embodiments, the therapeutically effective amount of unloaded thrombosomes forms clots at about 80% of the time platelets form. In some embodiments, the therapeutically effective amount of unloaded thrombosomes forms clots at about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80%.

In some embodiments, the therapeutically effective amount of unloaded thrombosomes forms clots at about 60% of the time platelets form clots in von Willebrand factor deficient plasma. In some embodiments, the therapeutically effective amount of unloaded thrombosomes forms clots at about 70% of the time platelets form clots in von Willebrand factor deficient plasma. In some embodiments, the therapeutically effective amount of unloaded thrombosomes forms clots at about 80% of the time platelets form in von Willebrand factor deficient plasma. In some embodiments, the therapeutically effective amount of unloaded thrombosomes forms clots at about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% in von Willebrand factor deficient plasma. In some embodiments, the therapeutically effective amount of unloaded thrombosomes (e.g., freeze-dried platelets) forms clots in von Willebrand deficient plasma.

In some embodiments, treatment of a subject with platelets loaded with an anti-fibrinolytic compound provides a "r" time (time to clot) that is shorter than the "r" time for treatment of the subject with the same amount of the free anti-fibrinolytic compound, that is, the anti-fibrinolytic compound that is not loaded into the platelets.

In some embodiments, treatment of a subject with thrombosomes loaded with an anti-fibrinolytic compound provides a "r" time (time to clot) that is shorter than the "r" time for treatment of the subject with the same amount of the free anti-fibrinolytic compound, that is, the anti-fibrinolytic compound that is not loaded into the thrombosomes.

The anti-fibrinolytic loaded platelets can be used in therapeutic applications as disclosed herein. For example, the anti-fibrinolytic loaded platelets can be used to treat von Willebrand disease (described herein).

Any known technique for drying platelets can be used in accordance with the present disclosure, as long as the technique can achieve a final residual moisture content of less than 5%. Preferably, the technique achieves a final residual moisture content of less than 2%, such as 1%, 0.5%, or 0.1%. Non-limiting examples of suitable techniques are freeze-drying (lyophilization) and spray-drying. A suitable lyophilization method is presented in Table A. Additional exemplary lyophilization methods can be found in U.S. Pat. Nos. 7,811,558, 8,486,617, and 8,097,403, each of which are incorporated herein by reference in their entireties. An exemplary spray-drying method includes: combining nitrogen, as a drying gas, with a loading buffer according to the present disclosure, then introducing the mixture into GEA Mobile Minor spray dryer from GEA Processing Engineering, Inc. (Columbia MD, USA), which has a Two-Fluid Nozzle configuration, spray drying the mixture at an inlet temperature in the range of 150° C. to 190° C., an outlet temperature in the range of 65° C. to 100° C., an atomic rate in the range of 0.5 to 2.0 bars, an atomic rate in the range of 5 to 13 kg/hr, a nitrogen use in the range of 60 to 100 kg/hr, and a run time of 10 to 35 minutes. The final step in spray drying is preferentially collecting the dried mixture. The dried composition in some embodiments is stable for at least six months at temperatures that range from −20° C. or lower to 90° C. or higher.

TABLE A

Exemplary Lyophilization Protocol

|  | Step | Temp. Set | Type | Duration | Pressure Set |
| --- | --- | --- | --- | --- | --- |
| Freezing Step | F1 | −50° C. | Ramp | Var | N/A |
|  | F2 | −50° C. | Hold | 3 Hrs | N/A |
| Vacuum Pulldown | F3 | −50° | Hold | Var | N/A |
| Primary Dry | P1 | −40° | Hold | 1.5 Hrs | 0 mT |
|  | P2 | −35° | Ramp | 2 Hrs | 0 mT |
|  | P3 | −25° | Ramp | 2 Hrs | 0 mT |
|  | P4 | −17° C. | Ramp | 2 Hrs | 0 mT |
|  | P5 | 0° C. | Ramp | 1.5 Hrs | 0 mT |
|  | P6 | 27° C. | Ramp | 1.5 Hrs | 0 mT |
|  | P7 | 27° C. | Hold | 16 Hrs | 0 mT |
| Secondary Dry | S1 | 27° C. | Hold | >8 Hrs | 0 mT |

In some embodiments, the step of drying the platelets that are obtained as disclosed herein, such as the step of freeze-drying the platelets that are obtained as disclosed herein, includes incubating the platelets with a lyophilizing agent to generate thrombosomes. In some embodiments, the lyophilizing agent is polysucrose. In some embodiments, the lyophilizing agent is a non-reducing disaccharide. Accordingly, in some embodiments, the methods for preparing thrombosomes from platelets further include incubating the platelets with a lyophilizing agent. In some embodiments, the lyophilizing agent is a saccharide. In some embodiments, the saccharide is a disaccharide, such as a non-reducing disaccharide.

In some embodiments, the platelets are incubated with a lyophilizing agent for a sufficient amount of time and at a suitable temperature to load the platelets with the lyophilizing agent. Non-limiting examples of suitable lyophilizing agents are saccharides, such as monosaccharides and disaccharides, including sucrose, maltose, trehalose, glucose (e.g., dextrose), mannose, and xylose. In some embodiments, non-limiting examples of lyophilizing agents include serum albumin, dextran, polyvinyl pyrrolidone (PVP), starch, and hydroxyethyl starch (HES). In some embodiments, exemplary lyophilizing agents can include a high molecular weight polymer, into the loading composition. By "high molecular weight" it is meant a polymer having an average molecular weight of about or above 70 kDa. Non-limiting examples are polymers of sucrose and epichlorohydrin. In some embodiments, the lyophilizing agent is polysucrose. Although any amount of high molecular weight polymer can be used as a lyophilizing agent, it is preferred that an amount be used that achieves a final concentration of about 3% to 10% (w/v), such as 3% to 7%, for example 6%.

In some embodiments, the process for preparing a composition includes adding an organic solvent, such as ethanol, to the loading solution. In such a loading solution, the solvent can range from 0.1% to 5.0% (v/v).

Within the process provided herein for making the compositions provided herein, addition of the lyophilizing agent can be the last step prior to drying. However, in some embodiments, the lyophilizing agent is added at the same time or before the anti-fibrinolytic, the cryoprotectant, or other components of the loading composition. In some embodiments, the lyophilizing agent is added to the loading solution, thoroughly mixed to form a drying solution, dispensed into a drying vessel (e.g., a glass or plastic serum vial, a lyophilization bag), and subjected to conditions that allow for drying of the solution to form a dried composition.

An exemplary saccharide for use in the compositions disclosed herein is trehalose. Regardless of the identity of the saccharide, it can be present in the composition in any suitable amount. For example, it can be present in an amount of 1 mM to 1 M. In embodiments, it is present in an amount of from 10 mM 10 to 500 mM. In some embodiments, it is present in an amount of from 20 mM to 200 mM. In some embodiments, it is present in an amount from 40 mM to 100 mM. In various embodiments, the saccharide is present in different specific concentrations within the ranges recited above, and one of skill in the art can immediately understand the various concentrations without the need to specifically recite each herein. Where more than one saccharide is present in the composition, each saccharide can be present in an amount according to the ranges and particular concentrations recited above.

The step of incubating the platelets to load them with a cryoprotectant or as a lyophilizing agent includes incubating the platelets for a time suitable for loading, as long as the time, taken in conjunction with the temperature, is sufficient for the cryoprotectant or lyophilizing agent to come into contact with the platelets and, preferably, be incorporated, at least to some extent, into the platelets. In embodiments, incubation is carried out for about 1 minute to about 180 minutes or longer.

The step of incubating the platelets to load them with a cryoprotectant or lyophilizing agent includes incubating the platelets and the cryoprotectant at a temperature that, when selected in conjunction with the amount of time allotted for loading, is suitable for loading. In general, the composition is incubated at a temperature above freezing for at least a sufficient time for the cryoprotectant or lyophilizing agent to come into contact with the platelets. In embodiments, incubation is conducted at 37° C. In certain embodiments, incubation is performed at 20° C. to 42° C. For example, in embodiments, incubation is performed at 35° C. to 40° C. (e.g., 37° C.) for 110 to 130 (e.g., 120) minutes.

In various embodiments, the bag is a gas-permeable bag configured to allow gases to pass through at least a portion or all portions of the bag during the processing. The gas-permeable bag can allow for the exchange of gas within the interior of the bag with atmospheric gas present in the surrounding environment. The gas-permeable bag can be permeable to gases, such as oxygen, nitrogen, water, air, hydrogen, and carbon dioxide, allowing gas exchange to occur in the compositions provided herein. In some embodiments, the gas-permeable bag allows for the removal of some of the carbon dioxide present within an interior of the bag by allowing the carbon dioxide to permeate through its wall. In some embodiments, the release of carbon dioxide from the bag can be advantageous to maintaining a desired pH level of the composition contained within the bag.

In some embodiments, the container of the process herein is a gas-permeable container that is closed or sealed. In some embodiments, the container is a container that is closed or sealed and a portion of which is gas-permeable. In some embodiments, the surface area of a gas-permeable portion of a closed or sealed container (e.g., bag) relative to the volume of the product being contained in the container (hereinafter referred to as the "SA/V ratio") can be adjusted to improve pH maintenance of the compositions provided herein. For example, in some embodiments, the SA/V ratio of the container can be at least about 2.0 $cm^2/mL$ (e.g., at least about 2.1 $cm^2/mL$, at least about 2.2 $cm^2/mL$, at least about 2.3 $cm^2/mL$, at least about 2.4 $cm^2/mL$, at least about 2.5 $cm^2/mL$, at least about 2.6 $cm^2/mL$, at least about 2.7 $cm^2/mL$, at least about 2.8 $cm^2/mL$, at least about 2.9 $cm^2/mL$, at least about 3.0 $cm^2/mL$, at least about 3.1 $cm^2/mL$, at least about 3.2 $cm^2/mL$, at least about 3.3 $cm^2/mL$, at least about 3.4 $cm^2/mL$, at least about 3.5 $cm^2/mL$, at least about 3.6 $cm^2/mL$, at least about 3.7 $cm^2/mL$, at least about 3.8 $cm^2/mL$, at least about 3.9 $cm^2/mL$, at least about 4.0 $cm^2/mL$, at least about 4.1 $cm^2/mL$, at least about 4.2 $cm^2/mL$, at least about 4.3 $cm^2/mL$, at least about 4.4 $cm^2/mL$, at least about 4.5 $cm^2/mL$, at least about 4.6 $cm^2/mL$, at least about 4.7 $cm^2/mL$, at least about 4.8 $cm^2/mL$, at least about 4.9 $cm^2/mL$, or at least about 5.0 $cm^2/mL$. In some embodiments, the SA/V ratio of the container can be at most about 10.0 $cm^2/mL$ (e.g., at most about 9.9 $cm^2/mL$, at most about 9.8 $cm^2/mL$, at most about 9.7 $cm^2/mL$, at most about 9.6 $cm^2/mL$, at most about 9.5 $cm^2/mL$, at most about 9.4 $cm^2/mL$, at most about 9.3 $cm^2/mL$, at most about 9.2 $cm^2/mL$, at most about 9.1 $cm^2/mL$, at most about 9.0 $cm^2/mL$, at most about 8.9 $cm^2/mL$, at most about 8.8 $cm^2/mL$, at most about 8.7 $cm^2/mL$, at most about 8.6, $cm^2/mL$ at most about 8.5 $cm^2/mL$, at most about 8.4 $cm^2/mL$, at most about 8.3 $cm^2/mL$, at most about 8.2 $cm^2/mL$, at most about 8.1 $cm^2/mL$, at most about 8.0 $cm^2/mL$, at most about 7.9 $cm^2/mL$, at most about 7.8 $cm^2/mL$, at most about 7.7 $cm^2/mL$, at most about 7.6 $cm^2/mL$, at most about 7.5 $cm^2/mL$, at most about 7.4 $cm^2/mL$, at most about 7.3 $cm^2/mL$, at most about 7.2 $cm^2/mL$, at most about 7.1 $cm^2/mL$, at most about 6.9 $cm^2/mL$, at most about 6.8 $cm^2/mL$, at most about 6.7 $cm^2/mL$, at most about 6.6 $cm^2/mL$, at most about 6.5 $cm^2/mL$, at most about 6.4 $cm^2/mL$, at most about 6.3 $cm^2/mL$, at most about 6.2 $cm^2/mL$, at most about 6.1 $cm^2/mL$, at most about 6.0 $cm^2/mL$, at most about 5.9 $cm^2/mL$, at most about 5.8 $cm^2/mL$, at most about 5.7 $cm^2/mL$, at most about 5.6 $cm^2/mL$, at most about 5.5 $cm^2/mL$, at most about 5.4 $cm^2/mL$, at most about 5.3 $cm^2/mL$, at most about 5.2 $cm^2/mL$, at most about 5.1 $cm^2/mL$, at most about 5.0 $cm^2/mL$, at most about 4.9 $cm^2/mL$, at most about 4.8 $cm^2/mL$, at most about 4.7 $cm^2/mL$, at most about 4.6 $cm^2/mL$, at most about 4.5 $cm^2/mL$, at most about 4.4 $cm^2/mL$, at most about 4.3 $cm^2/mL$, at most about 4.2 $cm^2/mL$, at most about 4.1 $cm^2/mL$, or at most about 4.0 $cm^2/mL$. In some embodiments, the SA/V ratio of the container can range from about 2.0 to about 10.0 $cm^2/mL$ (e.g., from about 2.1 $cm^2/mL$ to about 9.9 $cm^2/mL$, from about 2.2 $cm^2/mL$ to about 9.8 $cm^2/mL$, from about 2.3 $cm^2/mL$ to about 9.7 $cm^2/mL$, from about 2.4 $cm^2/mL$ to about 9.6 $cm^2/mL$, from about 2.5 $cm^2/mL$ to about 9.5 $cm^2/mL$, from about 2.6 $cm^2/mL$ to about 9.4 $cm^2/mL$, from about 2.7 $cm^2/mL$ to about 9.3 $cm^2/mL$, from about 2.8 $cm^2/mL$ to about 9.2 $cm^2/mL$, from about 2.9 $cm^2/mL$ to about 9.1 $cm^2/mL$, from about 3.0 $cm^2/mL$ to about 9.0 $cm^2/mL$, from about 3.1 $cm^2/mL$ to about 8.9 $cm^2/mL$, from about 3.2 $cm^2/mL$ to about 8.8 $cm^2/mL$, from about 3.3 $cm^2/mL$ to about 8.7 $cm^2/mL$, from about 3.4 $cm^2/mL$ to about 8.6 $cm^2/mL$, from about 3.5 $cm^2/mL$ to about 8.5 $cm^2/mL$, from about 3.6 $cm^2/mL$ to about 8.4 $cm^2/mL$, from about 3.7 $cm^2/mL$ to about 8.3 $cm^2/mL$, from about 3.8 $cm^2/mL$ to about 8.2 $cm^2/mL$, from about 3.9 $cm^2/mL$ to about 8.1 $cm^2/mL$, from about 4.0 $cm^2/mL$ to about 8.0 $cm^2/mL$, from about 4.1 $cm^2/mL$ to about 7.9 $cm^2/mL$, from about 4.2 $cm^2/mL$ to about 7.8 $cm^2/mL$, from about 4.3 $cm^2/mL$ to about 7.7 $cm^2/mL$, from about 4.4 $cm^2/mL$ to about 7.6 $cm^2/mL$, from about 4.5 $cm^2/mL$ to about 7.5 $cm^2/mL$, from about 4.6 $cm^2/mL$ to about 7.4 $cm^2/mL$, from about 4.7 $cm^2/mL$ to about 7.3 $cm^2/mL$, from about 4.8 $cm^2/mL$ to about 7.2 $cm^2/mL$, from about 4.9 $cm^2/mL$ to about 7.1 $cm^2/mL$, from about 5.0 $cm^2/mL$ to about 6.9 $cm^2/mL$, from about 5.1 $cm^2/mL$ to about 6.8 $cm^2/mL$, from about 5.2 $cm^2/mL$ to about 6.7 $cm^2/mL$, from about 5.3 $cm^2/mL$ to about 6.6 $cm^2/mL$, from about 5.4 $cm^2/mL$ to about 6.5 $cm^2/mL$, from about 5.5 $cm^2/mL$ to about 6.4 $cm^2/mL$, from about 5.6 $cm^2/mL$ to about 6.3 $cm^2/mL$, from about 5.7 $cm^2/mL$ to about 6.2 $cm^2/mL$, or from about 5.8 $cm^2/mL$ to about 6.1 $cm^2/mL$.

Gas-permeable closed containers (e.g., bags) or portions thereof can be made of one or more various gas-permeable materials. In some embodiments, the gas-permeable bag can be made of one or more polymers including fluoropolymers (such as polytetrafluoroethylene (PTFE) and perfluoroalkoxy (PFA) polymers), polyolefins (such as low-density polyethylene (LDPE), high-density polyethylene (HDPE)), fluorinated ethylene propylene (FEP), polystyrene, polyvinylchloride (PVC), silicone, and any combinations thereof.

In some embodiments, the lyophilizing agent as disclosed herein may be a high molecular weight polymer. By "high molecular weight" it is meant a polymer having an average molecular weight of about or above 70 kDa and up to 1,000,000 kDa Non-limiting examples are polymers of sucrose and epichlorohydrin (polysucrose). Although any amount of high molecular weight polymer can be used, it is preferred that an amount be used that achieves a final concentration of about 3% to 10% (w/v), such as 3% to 7%, for example 6%. Other non-limiting examples of lyoprotectants are serum albumin, dextran, polyvinyl pyrrolidone (PVP), starch, and hydroxyethyl starch (HES). In some embodiments, a lyoprotectant is also a cryoprotectant. For example, albumin, polysucrose, and sucrose can also be used as a cryoprotectant.

In some embodiments, lyophilized platelets can be fixed (e.g., lyophilized fixed plates) in a fixing agent. In some embodiments, lyophilized platelets can be fixed in formalin (e.g., lyophilized formalin-fixed platelets).

In some embodiments, the lyophilized platelets (e.g., thrombosomes) can be at a concentration from about 1,000 k/µl to about 500,000 k/µl. In some embodiments, the lyophilized platelets (e.g., thrombosomes) can be at a concentration from about 5,000 k/µl to about 450,000 k/µl. In some embodiments, the lyophilized platelets (e.g., thrombosomes) can be at a concentration from about 10,000 k/µl to about 400,000 k/µl. In some embodiments, the lyophilized platelets (e.g., thrombosomes) can be at a concentration from about 30,000 k/µl to about 300,000 k/µl. In some embodiments, the lyophilized platelets (e.g., thrombosomes) can be at a concentration from about 40,000 k/µl to about 250,000 k/µl. In some embodiments, the lyophilized platelets (e.g., thrombosomes) can be at a concentration from about 50,000 k/µl to about 225,000 k/µl. In some embodiments, the lyophilized platelets (e.g., thrombosomes) can be at a concentration from about 60,000 k/µl to about 200,000 k/µl. In some embodiments, the lyophilized platelets (e.g., thrombosomes) can be at a concentration from about 70,000 k/µl to about 175,000 k/µl. In some embodiments, the lyophilized platelets (e.g., thrombosomes) can be at a concentration from about 80,000 k/µl to about 150,000 k/µl. In some embodiments, the lyophilized platelets (e.g., thrombosomes) can be at a concentration from about 90,000 k/µl to about 125,000 k/µl. In some embodiments, the lyophilized platelets (e.g., thrombosomes) can be at a concentration from about 100,000 k/µl to about 120,000 k/µl. In some embodiments, the lyophilized platelets (e.g., thrombosomes) can be at a concentration from about 105,000 k/µl to about 115,000 k/µl. In some embodiments, the therapeutically effective amount of lyophilized platelets (e.g., thrombosomes) can be at any of the concentrations described herein).

In some embodiments, the lyophilized platelets (e.g., thrombosomes) can be at a concentration from about 1,000 to about 500,000 thrombosomes. In some embodiments, the lyophilized platelets (e.g., thrombosomes) can be at a concentration from about 5,000 to about 450,000 thrombosomes. In some embodiments, the lyophilized platelets (e.g., thrombosomes) can be at a concentration from about 10,000 to about 400,000 thrombosomes. In some embodiments, the lyophilized platelets (e.g., thrombosomes) can be at a concentration from about 30,000 to about 300,000 thrombosomes. In some embodiments, the lyophilized platelets (e.g., thrombosomes) can be at a concentration from about 40,000 to about 250,000 thrombosomes. In some embodiments, the lyophilized platelets (e.g., thrombosomes) can be at a concentration from about 50,000 thrombosomes to about 225,000 thrombosomes. In some embodiments, the lyophilized platelets (e.g., thrombosomes) can be at a concentration from about 60,000 to about 200,000 thrombosomes. In some embodiments, the lyophilized platelets (e.g., thrombosomes) can be at a concentration from about 70,000 thrombosomes to about 175,000 thrombosomes. In some embodiments, the lyophilized platelets (e.g., thrombosomes) can be at a concentration from about 80,000 to about 150,000 thrombosomes. In some embodiments, the lyophilized platelets (e.g., thrombosomes) can be at a concentration from about 90,000 to about 125,000 thrombosomes. In some embodiments, the lyophilized platelets (e.g., thrombosomes) can be at a concentration from about 100,000 thrombosomes to about 120,000 thrombosomes. In some embodiments, the lyophilized platelets (e.g., thrombosomes) can be at a concentration from about 105,000 to about 115,000 thrombosomes. In some embodiments, the therapeutically effective amount of lyophilized platelets (e.g., thrombosomes) can be at any of the concentrations described herein).

In some embodiments, the lyophilized platelets (e.g., thrombosomes) can be at a concentration from about $1 \times 10^2$ particles/kg to from about $1 \times 10^{13}$ particles/kg. In some embodiments, the lyophilized platelets (e.g., thrombosomes) can be at a concentration from about $1 \times 10^3$ particles/kg to from about $1 \times 10^{12}$ particles/kg. In some embodiments, the lyophilized platelets (e.g., thrombosomes) can be at a concentration from about $1 \times 10^4$ particles/kg to from about $1 \times 10^{11}$ particles/kg. In some embodiments, the lyophilized platelets (e.g., thrombosomes) can be at a concentration from about $1 \times 10^5$ particles/kg to from about $1 \times 10^{10}$ particles/kg. In some embodiments, the lyophilized platelets (e.g., thrombosomes) can be at a concentration from about $1 \times 10^6$ particles/kg to from about $1 \times 10^9$ particles/kg. In some embodiments, the lyophilized platelets (e.g., thrombosomes) can be at a concentration from about $1 \times 10^7$ particles/kg to from about $1 \times 10^8$ particles/kg. In some embodiments, a therapeutically effective amount of the lyophilized platelets (e.g., thrombosomes) can be at any of the concentrations described herein.

In some embodiments of the methods herein, any of the compositions described herein are administered topically. In some embodiments, topical administration can include administration via a solution, cream, gel, suspension, putty, particulates, or powder. In some embodiments, topical administration can include administration via a bandage (e.g. an adhesive bandage or a compression bandage) or medical closure (e.g., sutures, staples)); for example the anti-fibrinolytic loaded platelet derivatives (e.g., lyopreserved platelets (e.g., thrombosomes)) can be embedded therein or coated thereupon), as described in PCT Publication No. WO2017/040238 (e.g., paragraphs 8 013]-[069]), corresponding to U.S. patent application Ser. No. 15/776,255, the entirety of which is herein incorporated by reference.

In some embodiments of the methods herein, the compositions described herein are administered parenterally.

In some embodiments of the methods herein, the compositions described herein are administered intravenously.

In some embodiments of the methods herein, the compositions described herein are administered intramuscularly.

In some embodiments of the methods herein, the compositions described herein are administered intrathecally.

In some embodiments of the methods herein, the compositions described herein are administered subcutaneously.

In some embodiments of the methods herein, the compositions described herein are administered intraperitoneally. In some embodiments, the anti-fibrinolytic loaded platelets have a storage stability that is at least about equal to that of the platelets prior to the loading of the anti-fibrinolytic.

The loading buffer may be any buffer that is non-toxic to the platelets and provides adequate buffering capacity to the solution at the temperatures at which the solution will be exposed during the process provided herein. Thus, the buffer may include any of the known biologically compatible buffers available commercially, such as phosphate buffers, such as phosphate buffered saline (PBS), bicarbonate/carbonic acid, such as sodium-bicarbonate buffer, N-2-hydroxyethylpiperazine-N'-2-ethanesulfonic acid (HEPES), and tris-based buffers, such as tris-buffered saline (TB S). Likewise, it may include one or more of the following buffers: propane-1,2,3-tricarboxylic (tricarballylic); benzenepentacarboxylic; maleic; 2,2-dimethyl succinic; 3,3-dimethylglutaric; bis(2-hydroxyethyl)imino-tris(hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3 tetramethylene-glutaric acid); piperazine-1,4-bis-(2-ethanesulfonic acid) (PIPES); N-(2-acetamido)-2-amnoethanesulfonic acid (ACES); 1,1-cyclohexanediacetic; 3,6-endomethylene-1,2,3,6-tetrahydrophthalic acid (EMTA; ENDCA); imidazole; 2-(aminoethyl)trimethylammonium chloride (CHOLAMINE); N,N-bis(2-hydroxyethyl)-2-aminoethanesulfonic acid (BES); 2-methylpropane-1,2,3-triscarboxylic (beta-methyltricarballylic); 2-(N-morpholino)propanesulfonic acid (MOPS); phosphoric; and N-tris(hydroxymethyl)methyl-2-amminoethane sulfonic acid (TES).

A plate reader (e.g., Tecan Microplate reader (e.g., Infinite® 200 PRO)) can be used to quantify loading efficiency of the anti-fibrinolytic in the anti-fibrinolytic loaded platelets. Platelets can be evaluated for functionality by adenosine diphosphate (ADP), collagen, arachidonic acid, phorbol myristate acetate (PMA), thrombin receptor activating peptide (TRAP), and/or any other platelet agonist known in the art for stimulation post-loading. A hemostasis analyzer (e.g., TEG® 5000 Thromboelastogram® Hemostasis Analyzer system) can be used to test anti-fibrinolytic function of EACA loaded platelets.

In some embodiments, the anti-fibrinolytic platelets are lyophilized. In some embodiments, the anti-fibrinolytic loaded platelets are cryopreserved. In some embodiments, the unloaded platelets are lyophilized. In some embodiments, the unloaded platelets are cryopreserved.

In some embodiments, the anti-fibrinolytic loaded platelets retain the loaded anti-fibrinolytic compound upon rehydration and release the anti-fibrinolytic compound upon stimulation by endogenous platelet activators, such as endogenous platelet activators described herein.

In some embodiments, the dried platelets (such as freeze-dried platelets) retain the loaded anti-fibrinolytic upon rehydration and release the anti-fibrinolytic (e.g., EACA) upon stimulation by endogenous platelet activators. In some embodiments, at least about 10%, such as at least about 20%, such as at least about 30% of the anti-fibrinolytic is retained. In some embodiments, from about 10% to about 20%, such as from about 20% to about 30% of the anti-fibrinolytic is retained.

In some embodiments, anti-fibrinolytic loaded platelets, anti-fibrinolytic loaded platelet derivatives, or anti-fibrinolytic loaded thrombosomes can shield the anti-fibrinolytic from exposure in circulation, thereby reducing or eliminating systemic toxicity (e.g. cardiotoxicity) associated with the anti-fibrinolytic. In some embodiments, anti-fibrinolytic loaded platelets, anti-fibrinolytic loaded platelet derivatives, and/or anti-fibrinolytic loaded thrombosomes can also protect the anti-fibrinolytic from metabolic degradation or inactivation. In some embodiments, anti-fibrinolytic delivery with anti-fibrinolytic loaded platelets, anti-fibrinolytic loaded platelet derivatives, and/or anti-fibrinolytic loaded thrombosomes can therefore be advantageous in treatment of diseases such as von Willebrand disease or traumatic bleeding events (e.g., hemorrhage), since anti-fibrinolytic loaded platelets, anti-fibrinolytic loaded platelet derivatives, and/or anti-fibrinolytic loaded thrombosomes can mitigate systemic side effects. In some embodiments, anti-fibrinolytic loaded platelets, anti-fibrinolytic loaded platelet derivatives, and/or anti-fibrinolytic loaded thrombosomes can be used in any therapeutic setting in which expedited healing process is required or advantageous.

In some embodiments, provided herein is a method of treating a disease as disclosed herein in a subject in need thereof, comprising administering anti-fibrinolytic loaded platelets, anti-fibrinolytic loaded platelet derivatives, or anti-fibrinolytic loaded thrombosomes as disclosed herein. In some embodiments, provided herein is a method of treating a disease as disclosed herein in a subject in need thereof, comprising administering cold stored, room temperature stored, cryopreserved thawed, rehydrated, and/or lyophilized platelets, platelet derivatives, or thrombosomes as disclosed herein. In some embodiments, the disease is von Willebrand disease (e.g., any of the von Willebrand diseases disclosed herein).

In some embodiments, unloaded platelets, unloaded platelet derivatives, and/or unloaded thrombosomes can be advantageous in the treatment of a disease. In some embodiments, unloaded platelets, unloaded platelet derivatives, and/or unloaded thrombosomes can be advantageous in the treatment of diseases such as von Willebrand disease.

In some embodiments, provided herein is a method of treating a disease as disclosed herein in a subject in need thereof, (e.g., von Willebrand disease), comprising administering to a subject in need thereof, unloaded platelets, unloaded platelet derivatives, or unloaded thrombosomes as disclosed herein. In some embodiments, provided herein is a method of treating a disease as disclosed herein in a subject in need thereof, comprising administering unloaded cold stored, room temperature stored, cryopreserved thawed, rehydrated, and/or lyophilized platelets, unloaded platelet derivatives, or unloaded thrombosomes as disclosed herein.

While the embodiments of the methods and compositions described herein are amenable to various modifications and alternative forms, specific embodiments have been shown by way of example in the drawings and are described in detail below. The intention, however, is not to limit the methods and compositions to the particular embodiments described. On the contrary, the methods and compositions are intended to cover all modifications, equivalents, and alternatives falling within the scope of the methods and compositions as defined by the appended claims.

EXAMPLES

Example 1 Thrombosomes in Ristocetin Cofactor Assay

Thrombosomes were tested for their ability to bind von Willebrand factor (vWF) when incubated with ristocetin. The thrombosomes were compared to formalin-fixed platelets as a positive control (FIG. 1). Formalin-fixed platelets and thrombosomes were incubated with ristocetin and a small volume of pooled normal plasma. Agglutination was induced by adding plasma to platelets or thrombosomes and ristocetin. The data show that thrombosomes in the presence of ristocetin do not aggregate, unlike formalin-fixed platelets (FIG. 1). 6 different lots (A-F) of thrombosomes were tested and compared to the fixed platelets. The slope of the aggregation curve is used to assess the ristocetin co-factor assay, that is, it demonstrates the rate of vWF binding to GPIb. Using standardized platelet poor plasma, the assessment only depends on GPIb binding. The maximum response of thrombosomes was a slope of 15.92 verse 61.98 with fixed platelets. The data show that thrombosomes differ from fixed platelets in their ability to interact with vWF. Without wishing to be limited by any theory, the data suggest that vWF fails to sufficiently bind the GPIb receptor present on the thrombosomes, the GPIb receptor is absent and/or has reduced expression on thrombosomes, or is somehow otherwise inhibited from binding vWF.

Figure 2:
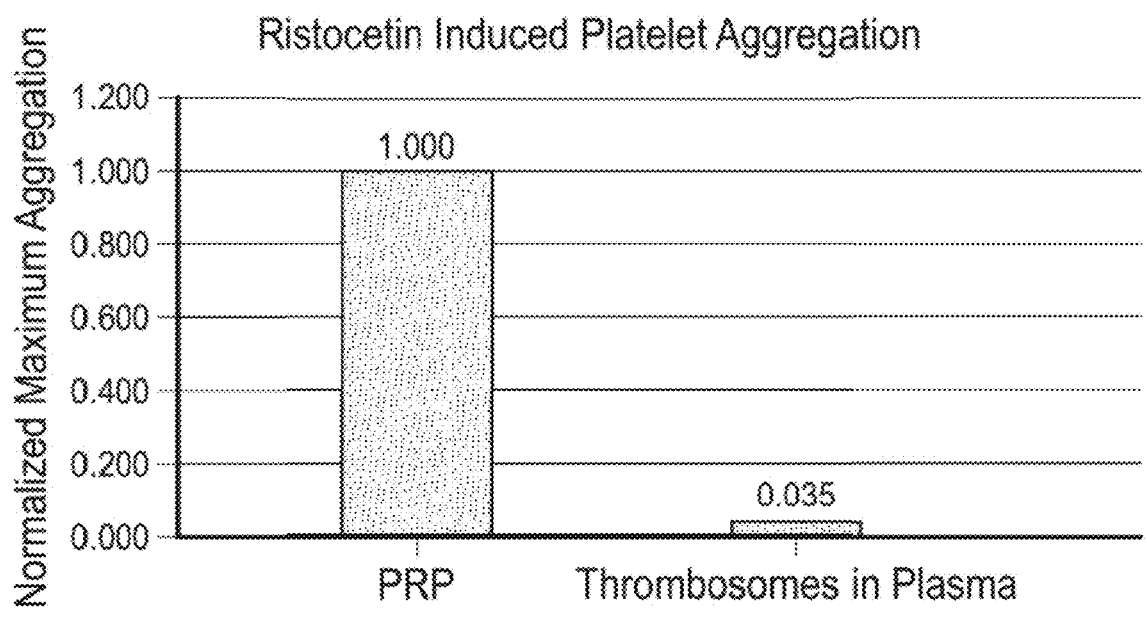
FIG. 2 is a graph showing aggregation of thrombosomes in plasma as compared to platelet rich plasma.

Additionally, thrombosomes were assessed for their ability to aggregate in plasma as compared to platelet rich plasma. The assay measures the capability of platelets and thrombosomes to be activated by ristocetin in plasma. Fresh drawn platelet rich plasma or thrombosomes in plasma are incubated with ristocetin. FIG. 2 shows that platelets in plasma were activated and aggregated, whereas thrombosomes in plasma did not activate and aggregate. The average platelet rich plasma aggregation was 48.4%, as compared to thrombosomes in plasma at 1.7%. The data represent thrombosomes as a percentage of "positive" group thrombosomes=1.7/48.4=3.5% magnitude vs platelet rich plasma. The data in FIG. 1 and FIG. 2 show that thrombosomes do not interact with vWF in a significant amount to cause aggregation in either the ristocetin co-factor assay or ristocetin-induced platelet activity assay, respectively. Without wishing to be bound by any theory, the lack of interaction between thrombosomes and vWF may be due to loss of GPIb (CD42b) receptor expression.

Figure 3:
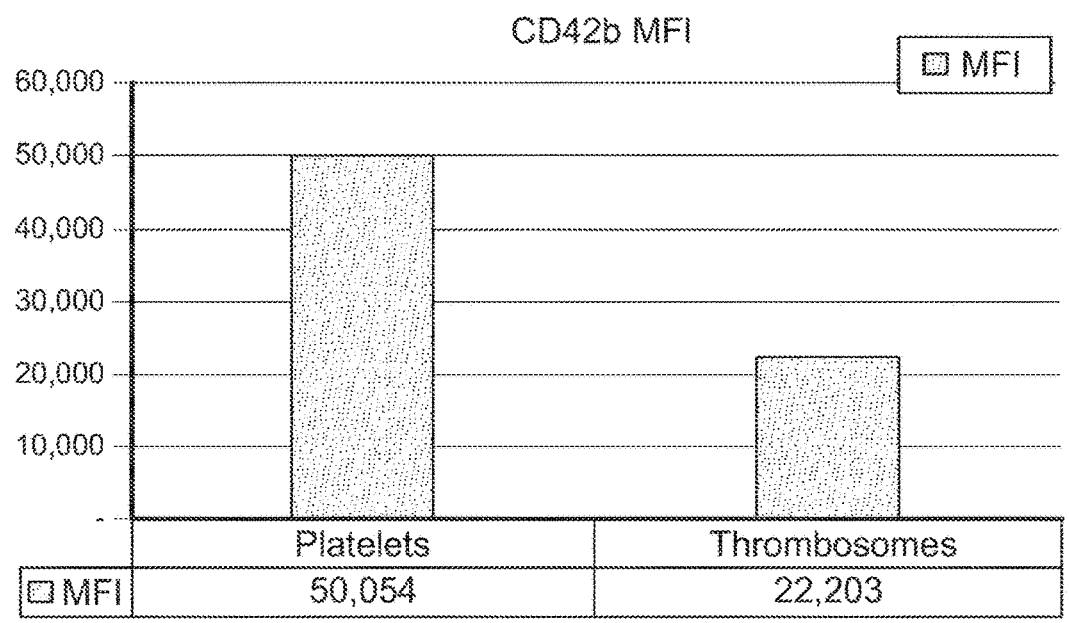
FIG. 3 is a graph showing CD42b expression in platelets as compared to thrombosomes.

CD42b is the portion of the CD42 protein receptor that binds vWF. Specific antibody clone AN51 also binds the CD42b domain of the receptor and can block vWF binding and subsequent tethering to collagen by platelets as reported by Dong et al., Ristocetin-dependent, but not botrocetin-dependent, binding of von Willebrand factor to the platelet glycoprotein $^1$b-IX-V complex correlates with shear-dependent interactions, *Blood,* 97, 162-168 (2001). AN51 antibody will inhibit both the Ristocetin Co-Factor assay (FIG. 1) and Ristocetin platelet activation assay (FIG. 2) mimicking the activity of thrombosomes. Flow cytometry staining of surface expression of CD42b thrombosomes are shown to express far less of this receptor as compared to normal platelets (FIG. 3). The data demonstrates another example of the lack of interaction between vWF and thrombosomes.

Protocol—Ristocetin Co-factor Assay

The Ristocetin Co-factor assay determines whether thrombosomes agglutinate in response to ristocetin+vWF. A positive response suggests intact, functional GP1bα receptors on the surface of the thrombosomes.

Materials/Reagents:
Helena Hemostasis Ristocetin Cofactor Assay (RCA) Kit (Cat #5370; Lot 2-18-5370)
  Lyophilized ristocetin (10 mg/mL reconstituted)
  Lyophilized formalin-fixed platelets
0.2 um filtered George King normal human plasma
Corning Cell Culture Grade 1×PBS
Corning Cell Culture Grade Water
Helena Laboratories AggRAM system (1-158-0000)
Aggregometer cuvettes
Aggregometer stir bars
Micropipettes & tips
1 unit Thrombosomes
Beckman-Coulter AcT diff 2 (1-418-0000)

Protocol:
1. Start the AggRAM as described in EQU-031 and perform the daily optical calibration check. There are ristocetin cofactor assay run settings built into the HemoRAM software. Use spin speed 600 rpm for all runs.
2. Bring RCA kit components to room temperature and rehydrate as indicated on the vial label.
   a. Reconstitute ristocetin with 1.5 mL water, swirl gently and allow to stand 10 minutes.
3. Prepare Thrombosomes samples by rehydrating Thrombosomes as indicated in PRO-022.
   a. Take 2×AcT counts of rehydrated Thrombosomes.
   b. Dilute aliquots washed Thrombosomes as needed to concentrations of:
      i. ~375 k/µL unwashed Thrombosomes in PBS.
      ii. ~375 k/µL washed Thrombosomes in PBS.
4. Prepare the 100% activity "blank" by diluting Thrombosomes 1:2 in PBS (final volume 250 µL) in an aggregometry cuvette with stir bar.
5. Prepare samples by adding 200 µL of Thrombosomes suspension to aggregometry cuvettes with stir bar.
6. Warm sample and blank cuvettes at 37° C. in the holding wells for 5 minutes prior to inserting in the aggregation wells.
7. Insert the "blank" cuvette into the first aggregation well and press the channel button. Allow to blank and replace with the first sample cuvette. Repeat for each sample/channel.
8. Add 25 µL ristocetin to the sample cuvette and press the channel button. Repeat for each sample, and allow to equilibrate 1 minute.
9. Add 25 µL filtered plasma to the sample cuvette and press the channel button. Repeat for each sample. Record runs for 5 minutes.
10. Export PDF of RCA TopChart output to appropriate file location.

Note: Formalin-fixed platelet positive controls were established at start of day to ensure ristocetin, GK plasma elicit appropriate agglutination response.

Sample Setup:

| Channel 1 | Channel 2 | Channel 3 | Channel 4 | Channel 5 | Channel 6 | Channel 7 | Channel 8 |
|---|---|---|---|---|---|---|---|
| Unwashed PBS | Unwashed Plasma | Unwashed Plasma | Unwashed Plasma | Washed PBS | Washed Plasma | Washed Plasma | Washed Plasma |

Volume each Thrombosomes dilution needed=[200(4)+125]*1.25=1.2 mL
Volume ristocetin needed per batch=8*25*1.25=250 µL
  (total 2×1.5 mL bottles rehydrated ristocetin for n=12)
Volume GK Plasma needed per batch=6*25*1.25=200
  (total 3×1 mL aliquots plasma filtered for n=12)
Total n=2 vials for each of 6 batches.

Flow Cytometry Assay:
Pooled apheresis platelet product (from 3 units, 24 hours post collection)
Standard Loading Buffer (pH 6.5-6.8)
30% Polysucrose
St Gobain VueLife 32C FEP bags
Wheaton 5 ml vials Manufacturing Disposables
Test Conditions:
Sublot A: Standard Thrombosomes®
Sublot B: CPP Optimized Thrombosomes®
Final formulation contains 1% DMSO, 1% Glycerol, and 10% Polysucrose Methods:
1. Acidify platelets to pH ~6.6 with citric acid. Centrifuge PRP at 1250 g for 20 min.
2. Re-suspend the platelet pellets in standard loading buffer. Target a count of $2500\times10^3$ plts/µl (prepare ~40 ml total).
3. Transfer the platelets to a FEP bag. Incubate at 37 C with agitation for 3 hours.
4. Add ¼ volume 30% Polysucrose to achieve 6% Polysucrose final concentration.
5. Take an aliquot from each sub-lot for pre-lyophilized testing. Each sub-lot will be tested by:
   a) Flow cytometry (surface markers, morphology, & count)
6. Fill each sub-lot into pre-labeled 5 ml vials with 1 ml fills. Add a stopper and transfer the vials to either the Stellar lyophilized with a pre-chilled shelf (−50 C) or the −80 C freezer shelf. Lyophilize the product using the following recipe:
   Freezing:
      Step 1: Ramp up to −50 C for 0 minutes.
      Step 2: −50 C for 180 minutes.
   Final Freezing:
      Shelf −40 C at 0 minutes; pressure at 0 mT.
   Primary Drying:
      1: Ramp shelf to −30 for 120 minutes (5 C/hr)
      Step 2: Hold shelf at −30 for 2880 minutes
      Step 3: Ramp shelf to −10 for 240 minutes (5 C/hr)
      Step 4: Hold shelf at −10 for 2880 minutes
      Step 3: Ramp shelf to +25 for 420 minutes (5 C/hr)
   Secondary Drying:
      Shelf 25° C. for 720 minutes; pressure at 0 mT.
      Shelf 25° C. at 9999 minutes; pressure at 0 mT. Hold for a minimum of 1 hour.
7. Stopper and cap all the vials following completion of the lyophilization cycle.
8. Bake at 80° C. for 24 hours.
9. Test 1 vial by:
   a) Flow cytometry (surface markers, morphology, & count)

Flow Protocol:
Counts
Goal—Determine the cell concentration of the pre-lyophilized material from each sub-lot
1. For each sub-lot prepare the following dilutions in duplicate.
2. For each pre-lyophilized sample add 10 µL of sample to 990 µL of PBS. Thoroughly mix the sample by pipetting before adding 100 µL of diluted sample to 900 µL of PBS. This will generate a pre-lyophilized sample with a final dilution factor of 1:1000.
3. Transfer 100 µL of each sample to an individual well on a 96 well plate.
4. Acquire each sample on the NovoCyte with the following conditions:
   a. Parameters: FSC, SSC
   b. Stop Conditions: 50 µL or 30,000 events
   c. FSC-H Threshold @1,000
   d. Absolute count dilution: 1,000
5. Determine the concentration of the platelet size population for each sample.

Size and Surface Marker Testing
This assay tests the size distribution and surface marker positivity of a sample at a standard concentration for the pre lyophilized material from each sub-lot. Additionally, each sample was single stained for CD42b using a PE conjugated anti-CD42b antibody (AN51).
1. Based on the flow count obtained in the previous section, create a 400 µL dilution of each sub-lot in PBS. The final count for each dilution should be 1,000,000 per µL.
2. For each sub-lot create the following 1:10 dilutions:
   a. Cells without calcium and GPRP: 225 µL HMTA+25 µL cells
   b. Cells with calcium and GPRP: 24 µL 150 mM $CaCl_2$+2 µL GPRP+199 µL HMTA+25 µL cells
3. Create HBS with 3 mM $CaCl_2$ by adding 160 µL of 150 mM $CaCl_2$ to 7,800 µL HBS.
4. Prepare staining mixes according to the tables below. This will provide enough antibody to stain the hIDSP and both sub-lots of pre-lyophilized material.

| CD62P Iso | |
|---|---|
| HN/ITA | 14 |
| Anti-CD41 PE | 84 |
| mIgG1 PECy5 | 35 |
| CD62P Test | |
| HN/ITA | 14 |
| Anti-CD41 PE | 84 |
| Anti-CD62P PECy5 | 35 |
| AV | |
| HMTA | 64 |
| Anti-CD41 PE | 156 |
| AV BV711 | 26 |

Figure 4:
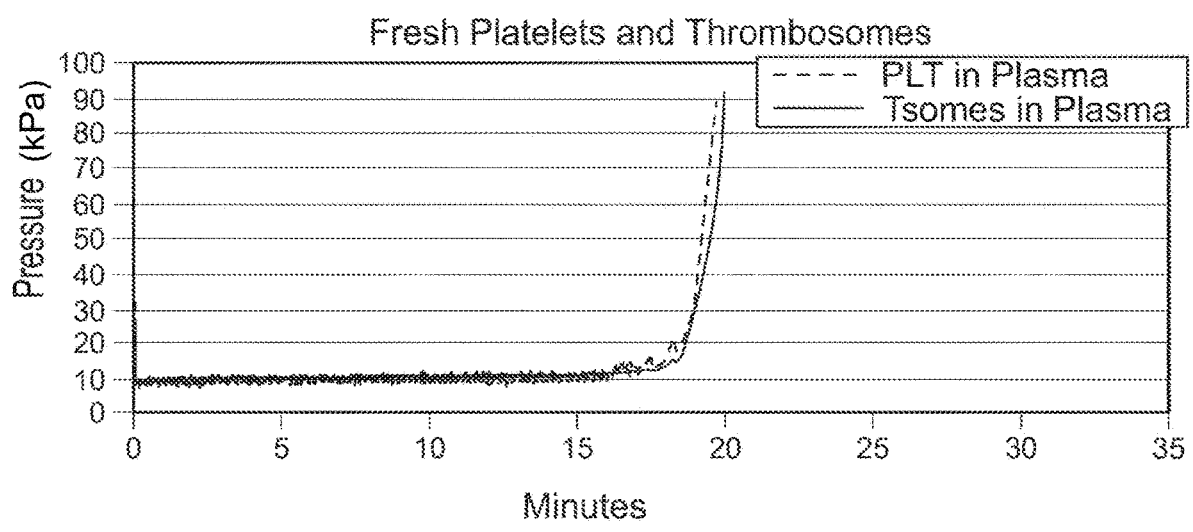
FIG. 4 is a graph showing T-TAS occlusion data under shear stress of platelets and thrombosomes in plasma.

5. Generate the following samples in duplicate for each pre-lyophilized sample:
   a. Unstained: 19 µL HMTA+5 µL cells
   b. CD62P Iso: 19 µL CD62P Iso mix+5 µL cells
   c. CD62P Test: 19 µL CD62P Test Mix+5 µL cells
   d. AV Neg: 19 µL AV Mix+5 µL cells
   e. AV Pos: 19 µL AV Mix+5 µL cells with calcium and GPRP
   f. CD42b: 17 µL HMTA+2 µL anti-CD42b+5 µL cells
6. Incubate all samples away from open light at room temperature for 20 minutes.
7. After incubation, add 400 µL HBS to each sample. Use HBS containing calcium to dilute AV test samples.
8. Transfer 100 µL of each sample to an individual well in a 96 well plate.
9. Acquire each sample on the NovoCyte with the following conditions:
   a. Parameters: FSC, SSC, B572, B660, V725
   b. Stop Conditions: 25 µL or 20,000 events
   c. FSC-H Threshold @1,000
   d. Flow Rate: Medium Example 2—Thrombosome Clotting In Vitro FIG. 4 shows that normal platelets and thrombosomes clot similarly under shear force upon exposure to collagen and tissue factor. Despite the limited interaction between vWF and thrombosomes (FIGS. 1-3), the limited interaction does not inhibit the ability of thrombosomes to form clots as measured by the T-TAS system. In the T-TAS system, thrombosomes and fresh platelets in normal plasma formed similar clots under shear forces stimulated by tissue factor and collagen coated channel (FIG. 4). The data supports that thrombosomes are capable of clot formation under shear stress and coagulation activation. The lack of aggregation by thrombosomes in the presence of ristocetin and yet normal clot formation demonstrate that thrombosomes can form clots in the absence of vWF.

Figure 5:
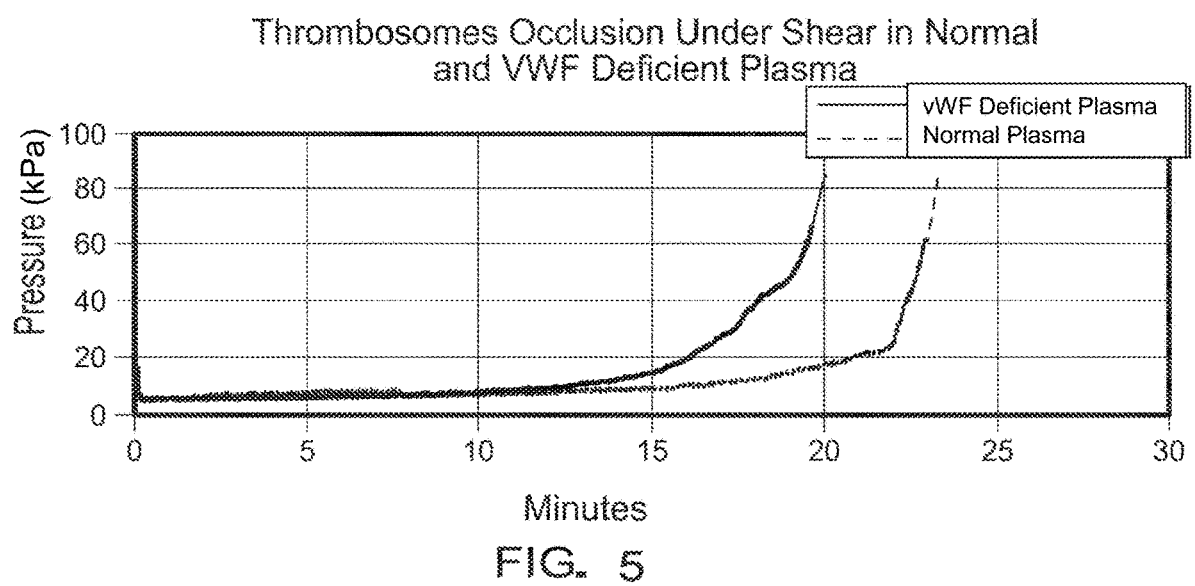
FIG. 5 is a graph showing T-TAS occlusion data under shear stress of thrombosomes in normal plasma and von Willebrand factor (vWF) deficient plasma.

Next, Thrombosomes were assayed for their ability to form clots in vWF deficient plasma. Thrombosomes in normal plasma cause occlusion of collagen and tissue factor channel on the AR chip as measured by the T-TAS system. Thrombosomes from the same lot were assayed with vWF deficient plasma and occluded similarly to normal plasma (FIG. 5), demonstrating Thrombosomes ability to form clots without the involvement of VWF.

The T-TAS® instrument was prepared for use according to the manufacturer's instructions. AR Chips (Diapharma Cat. #TC0101) and AR Chip Calcium Corn Trypsin Inhibitor (CaCTI; Diapharma Cat. #TR0101) were warmed to room temperature. 300 µL of rehydrated thrombosomes were transferred to a 1.7 mL microcentrifuge tube and centrifuged at 3900 g for 10 minutes to pellet. The thrombosomes pellet was resuspended in normal human plasma or autologous plasma with or without autologous platelets to a concentration of approximately 100,000-450,000 thrombosomes/µL, as determined by AcT counts (Beckman Coulter AcT Diff 2 Cell Counter). 20 µL of CaCTI with 480 µL of thrombosomes sample in plasma sample were mixed with gentle pipetting. The sample was loaded and ran on the T-TAS® according to the manufacturer's instructions.

Embodiments

Embodiment 1 is a method of treating von Willebrand disease in a subject, the method comprising: administering a therapeutically effective amount of unloaded thrombosomes to the subject in need thereof.

Embodiment 2 is a method of treating von Willebrand disease in a subject, the method comprising: administering a therapeutically effective amount of thrombosomes to the subject, wherein the method does not comprise administering an anti-fibrinolytic.

Embodiment 3 is the method of embodiment 1 or 2, wherein the von Willebrand disease is von Willebrand disease type 1, von Willebrand disease type 2, or von Willebrand disease type 3.

Embodiment 4 is the method of embodiment 1 or 2, wherein the von Willebrand disease is acquired von Willebrand disease.

Embodiment 5 is the method of any one of embodiments 1 to 4, wherein the concentration of the therapeutically effective amount of unloaded thrombosomes is from about $1 \times 10^2$ particles/kg to about $1 \times 10^{13}$ particles/kg.

Embodiment 6 is the method of any one of embodiments 1-5, wherein the concentration of the therapeutically effective amount of unloaded thrombosomes is from about $1 \times 10^4$ to about $1 \times 10^{11}$ particles/kg.

Embodiment 7 is the method of any one of embodiments 1-6, wherein the concentration of the therapeutically effective amount of unloaded thrombosomes is from about $1 \times 10^6$ to about $1 \times 10^9$ particles/kg.

Embodiment 8 is the method of any one of embodiments 1-4, wherein the concentration of the therapeutically effective amount of unloaded thrombosomes is at least $8.5 \times 10^8$ particles/kg.

Embodiment 9 is the method of any one of embodiments 1-4 and 8, wherein the concentration of the therapeutically effective amount of unloaded thrombosomes is at least $8.49 \times 10^9$ particles/kg.

Embodiment 10 is the method of any one of embodiments 1-9, wherein the surface expression of CD42b on the therapeutically effective amount of unloaded thrombosomes is about 50% less than the surface expression of CD42b on platelets.

Embodiment 11 is the method of any one of embodiments 1-10, wherein the surface expression of CD42b on the therapeutically effective amount of unloaded thrombosomes is about 40% less than the surface expression of CD42b on platelets.

Embodiment 12 is the method of any one of embodiments 1-11, wherein the surface expression of CD42b on the therapeutically effective amount of unloaded thrombosomes is about 25% less than the surface expression of CD42b on platelets.

Embodiment 13 is the method of any one of embodiments 1-12, wherein the therapeutically effective amount of unloaded thrombosomes forms clots in von Willebrand factor deficient plasma.

Embodiment 14 is the method of any one of embodiments 1-13, wherein the therapeutically effective amount of unloaded thrombosomes are administered topically.

Embodiment 15 is the method of any one of embodiments 1-13, wherein the therapeutically effective amount of unloaded thrombosomes are administered intravenously.

Embodiment 16 is the method of any one of embodiments 1-13, wherein the therapeutically effective amount of unloaded thrombosomes are administered intramuscularly.

Embodiment 17 is the method of any one of claims 1-13, wherein the therapeutically effective amount of unloaded thrombosomes are administered subcutaneously.

What is claimed is:

1. A method of treating von Willebrand disease in a subject, the method comprising:
   administering a therapeutically effective amount of freeze-dried platelet derivatives intravenously to the subject in need thereof, wherein the plasma of the subject is deficient in von Willebrand factor, and the therapeutically effective amount of freeze-dried platelet derivatives is an amount sufficient to form clots in plasma of the subject, wherein the therapeutically effective amount of freeze-dried platelet derivatives is at least $8.5 \times 10^8$ particles/kg of the subject, and wherein the surface expression of CD42b on the freeze-dried platelet derivatives is between 25% and 50% of the surface expression of CD42b on normal platelets, and wherein the freeze-dried platelet derivatives are loaded with an anti-fibrinolytic agent selected from ε-aminocaproic acid, aprotinin, aminomethylbenzoic acid, tranexamic acid, and fibrinogen.

2. The method of claim 1, wherein the von Willebrand disease is von Willebrand disease type 1, von Willebrand disease type 2, or von Willebrand disease type 3.

3. The method of claim 1, wherein the von Willebrand disease is acquired von Willebrand disease.

4. The method of claim 1, wherein the surface expression of CD42b on the therapeutically effective amount of freeze-dried platelet derivatives is between 30% and 50% of the surface expression of CD42b on normal platelets.

5. The method of claim 1, wherein the anti-fibrinolytic agent is ε-aminocaproic acid.

6. The method of claim 5, wherein the freeze-dried platelet derivatives provide a time to clot that is shorter than the time to clot for treatment of the subject with the same amount of a free anti-fibrinolytic compound that is not loaded into the freeze-dried platelet derivatives.

7. The method of claim 1, wherein the anti-fibrinolytic agent is one of ε-aminocaproic acid, aprotinin, aminomethylbenzoic acid, and tranexamic acid.

8. The method of claim 7, wherein the therapeutically effective amount of freeze-dried platelet derivatives is at least $8.49 \times 10^9$ particles/kg.

9. The method of claim 7, wherein the surface expression of CD42b on the therapeutically effective amount of freeze-dried platelet derivatives is between 40% and 50% of the surface expression of CD42b on normal platelets.

10. The method of claim 7, wherein the surface expression of CD42b on the therapeutically effective amount of freeze-dried platelet derivatives is between 40% and 50% of the surface expression of CD42b on normal platelets, and wherein the therapeutically effective amount of freeze-dried platelet derivatives is at least $8.49 \times 10^9$ particles/kg.

11. The method of claim 7, wherein the therapeutically effective amount of freeze-dried platelet derivatives forms clots in von Willebrand factor deficient plasma in from about 70% to about the same time as in normal plasma.

12. The method of claim 11, wherein the therapeutically effective amount of freeze-dried platelet derivatives forms clots in von Willebrand factor deficient plasma in about 70% to about 80% of the time as in normal plasma.

13. The method of claim 7, wherein the freeze-dried platelet derivatives provide a time to clot that is shorter than the time to clot for treatment of the subject with the same amount of a free anti-fibrinolytic compound that is not loaded into the freeze-dried platelet derivatives.

14. The method of claim 7, wherein the surface expression of CD42b on the therapeutically effective amount of freeze-dried platelet derivatives is between 30% and 50% of the surface expression of CD42b on normal platelets.

15. The method of claim 7, wherein the freeze-dried platelet derivatives have less than 10% crosslinking of platelet membranes via proteins and/or lipids present on the membranes.

16. The method of claim 7, wherein at least 60% of the freeze-dried platelet derivatives have a particle size in the range of 0.3 μm to 5.0 μm.

17. A method of treating a coagulopathy in a subject, wherein the coagulopathy is caused by von Willebrand disease, the method comprising administering intravenously to the subject in need thereof a therapeutically effective amount of a composition comprising freeze-dried platelet derivatives and an incubating agent comprising one or more salts, a buffer, and a cryoprotectant, wherein the composition is administered to the subject having von Willebrand disease, wherein the plasma of the subject is deficient in von Willebrand factor, and the freeze-dried platelet derivatives in the composition is an amount sufficient to form clots in plasma of the subject, wherein the therapeutically effective amount of the composition is at least $8.5 \times 10^8$ particles/kg of the subject, wherein the surface expression of CD42b on the freeze-dried platelet derivatives is between 25% and 50% of the surface expression of CD42b on normal platelets, and wherein the freeze-dried platelet derivatives are loaded with an anti-fibrinolytic agent selected from ε-aminocaproic acid, aprotinin, aminomethylbenzoic acid, tranexamic acid, and fibrinogen.

18. The method of claim 17, wherein the von Willebrand disease is von Willebrand disease type 1, von Willebrand disease type 2, von Willebrand disease type 3, or acquired von Willebrand disease.

19. The method of claim 17, wherein the incubating agent comprises an organic solvent and a saccharide comprising trehalose, and wherein the cryoprotectant comprises polysucrose in a concentration of 3 to 10% (w/v).

20. The method of claim 17, wherein the surface expression of CD42b on the freeze-dried platelet derivatives in the therapeutically effective amount of the composition is between 30% and 50% of the surface expression of CD42b on normal platelets, and wherein the anti-fibrinolytic agent is selected from ε-aminocaproic acid, aprotinin, aminomethylbenzoic acid, and tranexamic acid.

* * * * *